(12) United States Patent
Zhao

(10) Patent No.: US 6,838,528 B2
(45) Date of Patent: Jan. 4, 2005

(54) MULTI-ARM BLOCK COPOLYMERS AS DRUG DELIVERY VEHICLES

(75) Inventor: Xuan Zhao, Huntsville, AL (US)

(73) Assignee: Nektar Therapeutics AL, Corporation, Huntsville, AL (US)

(*) Notice: Subject to any disclaimer, the term of this patent is extended or adjusted under 35 U.S.C. 154(b) by 0 days.

(21) Appl. No.: 10/795,913

(22) Filed: Mar. 8, 2004

(65) Prior Publication Data

US 2004/0170595 A1 Sep. 2, 2004

Related U.S. Application Data

(62) Division of application No. 10/054,662, filed on Jan. 22, 2002, now Pat. No. 6,730,334.
(60) Provisional application No. 60/262,754, filed on Jan. 19, 2001.

(51) Int. Cl.⁷ .................. C08F 283/00; C08G 63/91; A61K 31/80; A61K 31/74; A61F 2/00
(52) U.S. Cl. ............ 525/419; 525/231; 525/326.9; 525/328.8; 528/354; 528/425; 424/783; 424/422; 424/78.08
(58) Field of Search .................... 525/419, 231, 525/326.9, 328.8; 528/354, 425; 424/783, 422, 78.08

(56) References Cited

U.S. PATENT DOCUMENTS

| | | | |
|---|---|---|---|
| 3,101,374 A | 8/1963 | Patton, Jr. | |
| 4,278,555 A | 7/1981 | Zaweski et al. | |
| 4,894,238 A | 1/1990 | Embry et al. | |
| 5,135,751 A | 8/1992 | Henry et al. | |
| 5,306,501 A | 4/1994 | Viegas et al. | |
| 5,429,826 A | 7/1995 | Nair et al. | |
| 5,543,158 A | 8/1996 | Gref et al. | |
| 5,610,241 A | 3/1997 | Lee et al. | |
| 5,618,528 A | 4/1997 | Cooper et al. | |

(List continued on next page.)

FOREIGN PATENT DOCUMENTS

| | | |
|---|---|---|
| EP | 0 462 408 A2 | 12/1991 |
| EP | 0 473 268 A2 | 3/1992 |
| WO | WO 92/00748 A1 | 1/1992 |
| WO | WO 96/03984 | 2/1996 |
| WO | WO 99/29303 A1 | 6/1999 |
| WO | WO 99/45964 | 9/1999 |
| WO | WO 00/65024 A3 | 11/2000 |
| WO | WO 01/49268 A1 | 7/2001 |

OTHER PUBLICATIONS

Choi et al., "Star–Shaped Poly(ether–ester) Block Copolymers: Synthesis, Characterization, and Their Physical Properties", *Macromolecules*, 1998, pp. 8766–8774, vol. 31, No. 25.

(List continued on next page.)

*Primary Examiner*—Duc Truong
(74) *Attorney, Agent, or Firm*—Alston & Bird LLP

(57) ABSTRACT

The invention provides multi-arm block copolymers useful as drug delivery vehicles comprising a central core molecule, such as a residue of a polyol, and at least three copolymer arms covalently attached to the central core molecule, each copolymer arm comprising an inner hydrophobic polymer segment covalently attached to the central core molecule and an outer hydrophilic polymer segment covalently attached to the hydrophobic polymer segment, wherein the central core molecule and the hydrophobic polymer segment define a hydrophobic core region. The solubility of hydrophobic biologically active agents can be improved by entrapment within the hydrophobic core region of the block copolymer. The invention further includes pharmaceutical compositions including such block copolymers, methods of making such copolymers and pharmaceutical compositions, and methods of using the block copolymers as drug delivery vehicles.

38 Claims, 6 Drawing Sheets

U.S. PATENT DOCUMENTS

| | | | |
|---|---|---|---|
| 5,672,662 | A | 9/1997 | Harris et al. |
| 5,681,576 | A | 10/1997 | Henry |
| 5,874,500 | A | 2/1999 | Rhee et al. |
| 5,932,462 | A | 8/1999 | Harris et al. |
| 5,965,566 | A | 10/1999 | Greenwald et al. |
| 6,011,042 | A | 1/2000 | Greenwald et al. |
| 6,051,648 | A | 4/2000 | Rhee et al. |
| 6,096,331 | A | 8/2000 | Desai et al. |
| 6,166,130 | A | 12/2000 | Rhee et al. |
| 6,210,717 | B1 | 4/2001 | Choi et al. |
| 6,258,351 | B1 | 7/2001 | Harris |
| 6,323,278 | B2 | 11/2001 | Rhee et al. |
| 6,328,988 | B1 | 12/2001 | Uhrich |
| 6,348,558 | B1 | 2/2002 | Harris et al. |
| 6,362,276 | B1 | 3/2002 | Harris et al. |
| 6,436,425 | B1 | 8/2002 | Henry et al. |
| 6,497,895 | B2 | 12/2002 | Uhrich |
| 6,515,100 | B2 | 2/2003 | Harris |
| 2002/0013408 | A1 | 1/2002 | Rhee et al. |
| 2002/0041898 | A1 | 4/2002 | Unger et al. |
| 2003/0059465 | A1 | 3/2003 | Unger et al. |
| 2004/0009229 | A1 | 1/2004 | Unger et al. |

OTHER PUBLICATIONS

Choi, Young Kweon, "Biodegradable Star–Shaped Block Copolymer Hydrogels for Drug Delivery", Dissertation, The University of Utah, Department of Pharmaceutics and Pharmaceutical Chemistry, Jun. 1996, pp. 1–229.

Gayet, J.–C., and G. Fortier, "High Water Content BSA–PEG Hydrogel for Controlled Release Device: Evaluation of the Drug Release Properties," *Journal of Controlled Release*, 1996, pp. 177–184, vol. 38.

Harris, J. Milton, "Introduction to Biotechnical and Biomedical Applications of Poly(Ethylene Glycol)", *Poly(Ethylene Glycol) Chemistry: Biotechnical and Biomedical Applications*, 1992, pp. 1–14.

Jain et al., "Controlled release of drugs from injectable in situ formed biodegradable PLGA microspheres: effect of various formulation variables", *European Journal of Pharmaceutics and Biopharmaceutics*, 2000, pp. 257–262, vol. 50, No. 2.

Jeong et al., "Adriamycin release from flower–type polymeric micelle based on star–block copolymer composed of poly($\gamma$–benzyl L–glutamate) as the hydrophobic part and poly(ethylene oxide) as the hydrophilic part", *International Journal of Pharmaceutics*, 1999, pp. 49–58, vol. 188.

Jeong et al., "New biodegradable polymers for injectable drug delivery systems", *Journal of Controlled Release*, 1999, pp. 109–114, vol. 62.

Jeong, B., et al., "Biodegradable Block Copolymers as Injectable Drug–Delivery Systems," *Nature*, 1997, pp. 860–862, vol. 388.

Lewis, Richard J., Sr., *Hawley's Condensed Chemical Dictionary*, 1997, pp. 891–892 and 1092–1093, Thirteenth Edition, John Wiley & Sons, Inc.

Liu et al., "Water–soluble dendritic unimolecular micelles: Their potential as drug delivery agents", *Journal of Controlled Release*, 2000, pp. 121–131, vol. 65.

Piskin et al., "Novel PDLLA/PEG copolymer micelles as drug carriers", *J. Biomater. Sci. Polymer Edn*, 1995, pp. 359–373, vol. 7, No. 4.

Pistel et al., "Biodegradable recombinant human erythropoietin loaded microspheres prepared from linear and star–branched block copolymers: Influence of encapsulation technique and polymer composition on particle characteristics", *Journal of Controlled Release*, 1999, pp. 309–325, vol. 59.

Roubi, Maureen, "Hyperbranched polymers deliver drugs steadily", *Chemical & Engineering News*, 1999, p. 63, vol. 77, No. 03.

Sawhney, A., et al., "Bioerodible Hydrogels Based on Photopolymerized Poly(ethylene glycol)–co–poly($\alpha$–hydroxy acid) Diacrylate Macromers," *Macromolecules*, 1993, pp. 581–587, vol. 26.

Schmalenberg et al., "Cytotoxicity of a Unimolecular Polymeric Micelle and Its Degradation Products", *Biomacromolecules*, 2001, pp. A–E.

Yasugi et al., "Preparation and characterization of polymer micelles from poly(ethylene glycol)–poly(D,L–lactide) block copolymers as potential drug carrier", *Journal of Controlled Release*, 1999, pp. 89–100, vol. 62.

Yu et al., "Polymeric micelles for drug delivery: solubilization and haemolytic activity of amphotericin B", *Journal of Controlled Release*, 1998, pp. 131–136, vol. 53.

Zalipsky et al., "Attachment of Drugs to Polyethylene Glycols", *Eur. Polym. J.*, 1983, pp. 1177–1183, vol. 19, No. 12.

Zalipsky, Samuel, "Chemistry of polyethylene glycol conjugates with biologically active molecules", *Advanced Drug Reviews*, 1995, pp. 157–182, vol. 16.

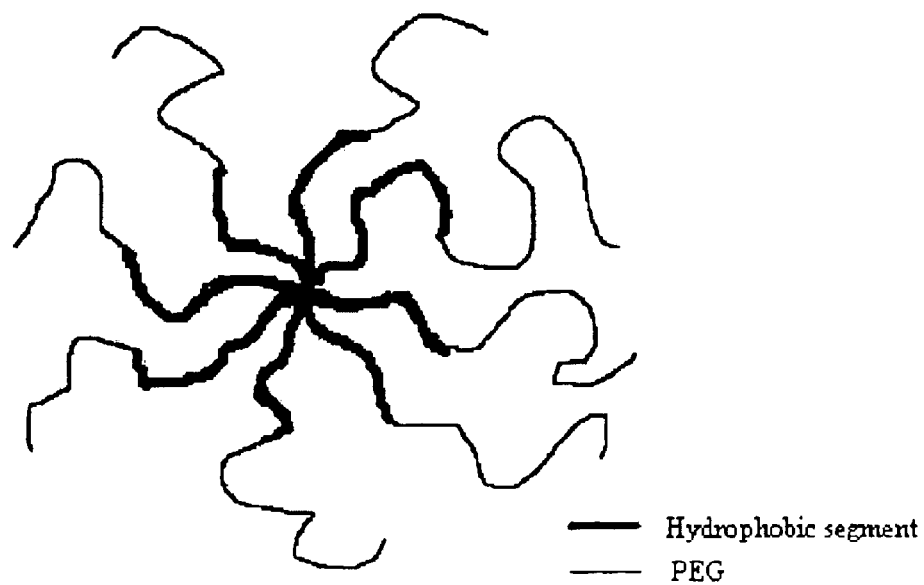
— Hydrophobic segment
—— PEG
Figure 1
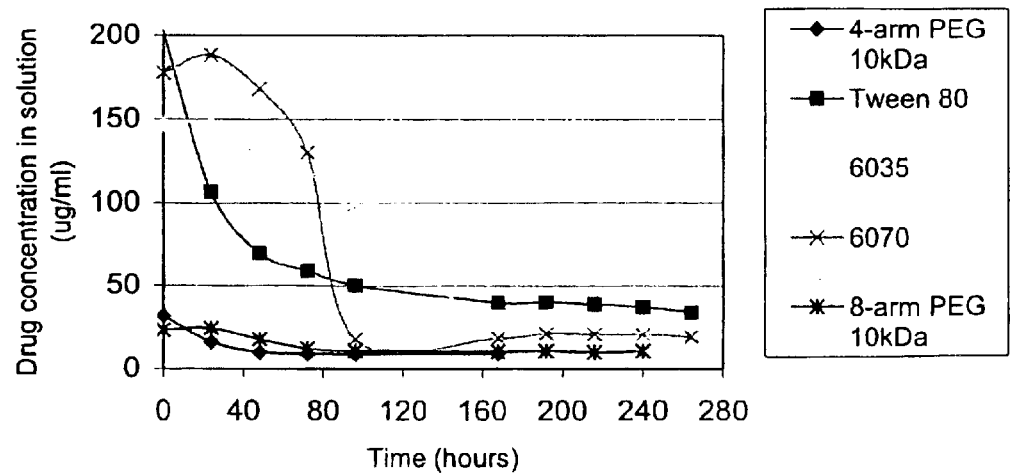

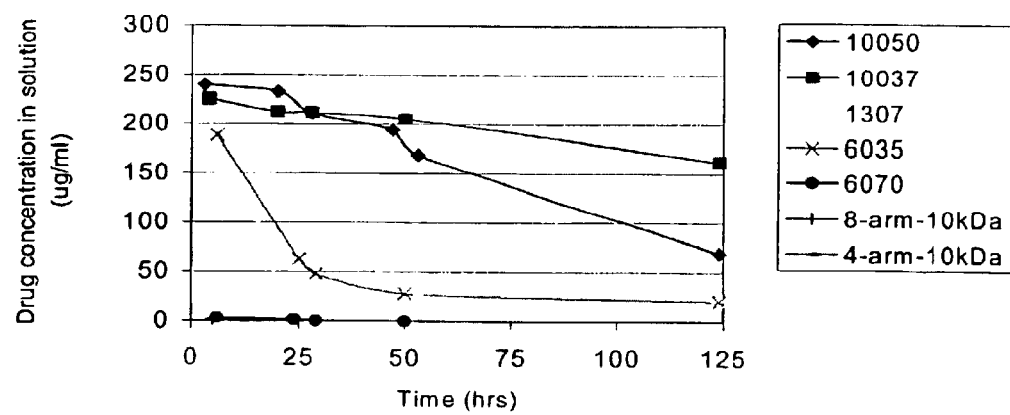
Figure 3: Release profile of simvastatin in aqueous solutions at pH 7
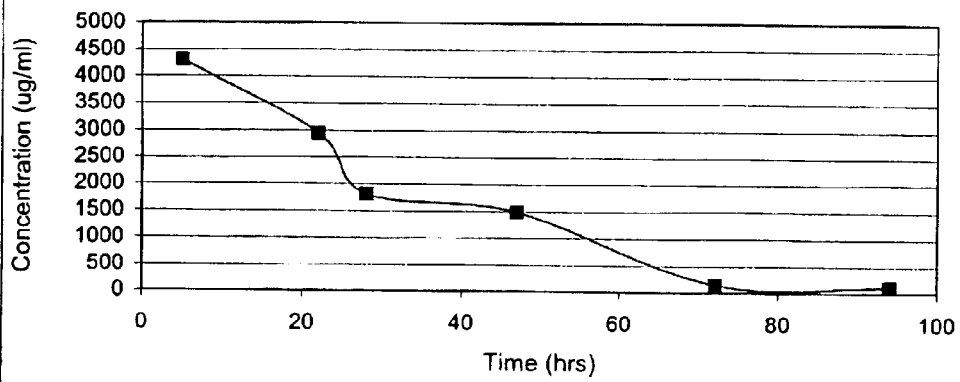
Figure 4: Release Profile of Simvastatin From Bisphosphonate Derivative of PPO-PEG 10050 in pH 7.0

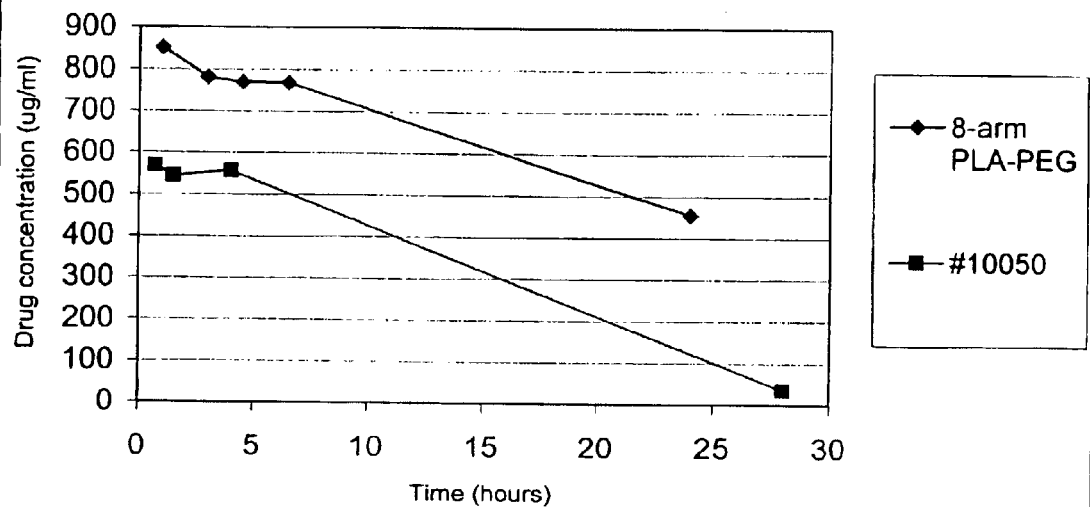
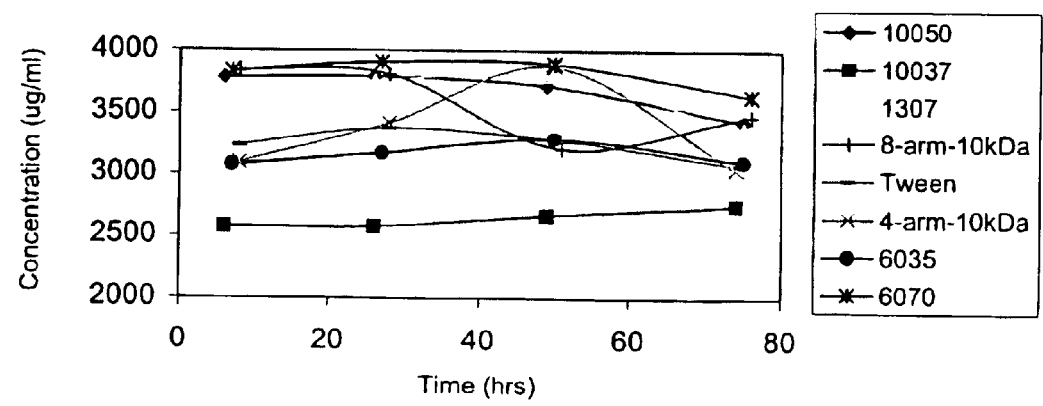

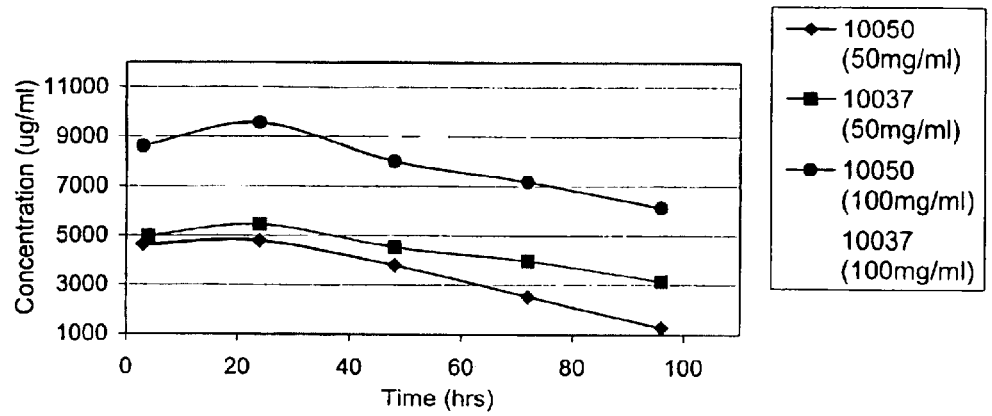
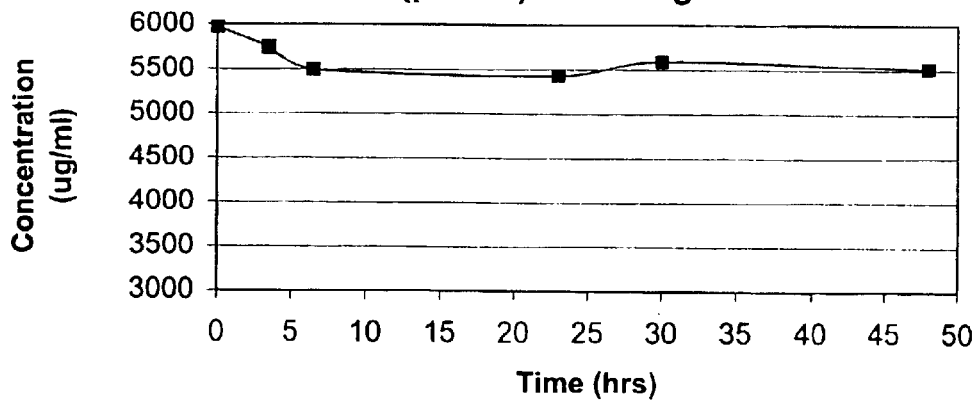

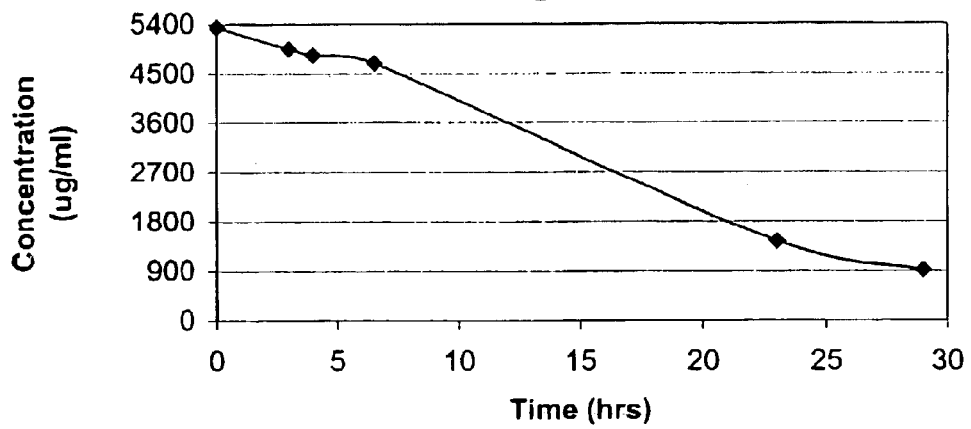
Figure 9: Release profile of paclitaxel solubilized by 8-arm-PCL-PEG2$_{6kDa}$ in phosphate buffer (pH 7.0) at 37 deg. C
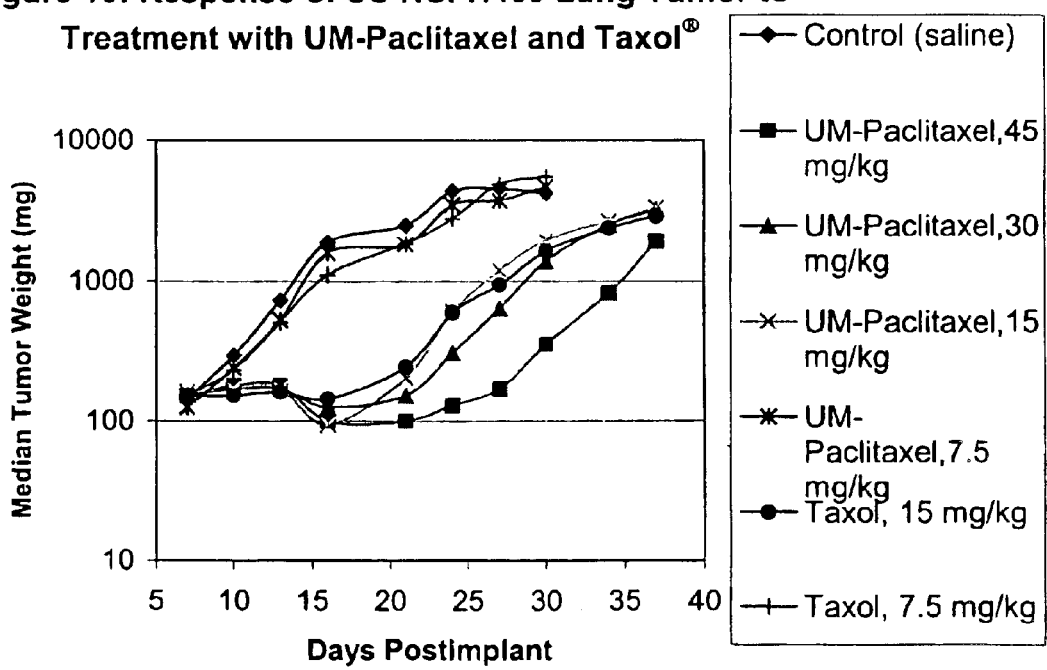
Figure 10: Response of SC NCI-H460 Lung Tumor to Treatment with UM-Paclitaxel and Taxol®

| HG[PCL-PEG3k2] by dialysis (Combined) |  |
|---|---|
| Effective Diameter: | 19.6 nm |
| Polydispersity: | 0.064 |
| Avg. Count Rate: | 71.3 kcps |
| Sample Quality: | 9.3/100.00% |
| Elapsed Time: | 00:12:00 |

| Run | Eff. Diam. (nm) | Half Width (nm) | Polydispersity | Sample Quality |
|---|---|---|---|---|
| 1 | 20.1 | 5.5 | 0.075 | 8.6/100.00% |
| 2 | 19.7 | 5.7 | 0.082 | 9.3/100.00% |
| 3 | 19.3 | 5.4 | 0.077 | 9.7/100.00% |
| 4 | 19.1 | 5.5 | 0.082 | 9.6/100.00% |
| 5 | 19.5 | 3.9 | 0.040 | 8.8/100.00% |
| 6 | 19.5 | 4.1 | 0.044 | 9.7/100.00% |
| Mean | 19.5 | 5.0 | 0.067 | 9.3/100.00% |
| Std. Error | 0.1 | 0.3 | 0.008 | 0.2/ 0.00 |
| Combined | 19.6 | 4.9 | 0.064 | 9.3/100.00% |

MULTI-ARM BLOCK COPOLYMERS AS DRUG DELIVERY VEHICLES

CROSS-REFERENCE TO RELATED APPLICATIONS

This application is a divisional of U.S. application Ser. No. 10/054,662, filed Jan. 22, 2002, now U.S. Pat. No. 6,730,334 which claims the benefit of U.S. Provisional Application No. 60/262,754, filed Jan. 19, 2001, both of which are incorporated herein by reference in their entirety.

FIELD OF THE INVENTION

The invention relates to multi-arm copolymers containing a hydrophobic core region and a hydrophilic outer region, methods of making such copolymers, and methods of using such copolymers as drug delivery vehicles.

BACKGROUND OF THE INVENTION

Solubilization and delivery of hydrophobic drugs is one of the most challenging issues in pharmaceutical formulation, particularly since most drugs are hydrophobic. Such drugs tend to precipitate in an aqueous environment, such as the bloodstream. Whether the drug is delivered by oral or parenteral routes, a certain level of aqueous solubility is required for adequate absorption and bioavailability. Pharmaceutical grade surfactants, such as Tween® 80 or Cremophor®, have been widely used in formulations to compensate for the low aqueous solubility of hydrophobic drugs. These surfactants solubilize hydrophobic drugs by forming micellar structures in aqueous media. Unfortunately, these surfactants have been associated with severe allergic reactions and hypersensitivity when administered to patients (Kris, et al., Cancer Treatment REP, 70:5, (1986)). After parenteral administration, these micellar drug carriers disintegrate when the concentration is below their critical micelle concentration (CMC), resulting in a rapid release of the drug. That is to say, in addition to the possibility of adverse side effects upon administration, conventional surfactant-based carriers also lack the ability to provide controlled release of a drug.

Thus, there remains a need in the art for a method for imparting adequate levels of aqueous solubility to a hydrophobic drug such that the drug may be administered in a therapeutically effective manner.

SUMMARY OF THE INVENTION

The invention is directed to multi-arm block copolymers useful as drug delivery vehicles. The multi-arm block copolymers comprise a central core molecule, such as a residue of a polyol, and at least three copolymer arms covalently attached to the central core molecule, each copolymer arm comprising an inner hydrophobic polymer segment covalently attached to the central core molecule and an outer hydrophilic polymer segment covalently attached to the hydrophobic polymer segment. The block copolymer provides a unimolecular micelle structure, wherein the central core molecule and the hydrophobic polymer segment define a hydrophobic core region and the hydrophilic polymer segment defines an outer hydrophilic region. The solubility of hydrophobic biologically active agents can be improved by entrapment within the hydrophobic core region of the block copolymer. Thus, improved delivery of hydrophobic drugs can be obtained by administering a pharmaceutical composition to a mammal, the pharmaceutical composition comprising a multi-arm block copolymer of the invention having a drug entrapped within the hydrophobic core region thereof.

BRIEF DESCRIPTION OF THE DRAWINGS

Figure 11:
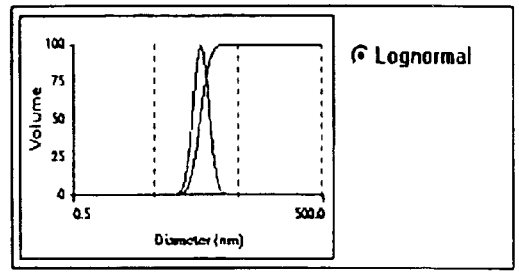

Having thus described the invention in general terms, reference will now be made to the accompanying figures, wherein:

FIG. 1 is an illustration of the structure of an embodiment of the multi-arm block copolymer of the invention;

FIG. 2 provides release profiles for the drug, 3,4-di-[1-methyl 6-nitro-3-indolyl]-1H-pyrrole-2,5-dione (MNIPD), in several polymer compositions;

FIG. 3 provides release profiles for the drug, simvastatin, in several polymer compositions;

FIG. 4 provides a release profile for simvastatin in an exemplary bisphosphonate derivative of a multi-arm block copolymer;

FIG. 5 provides release profiles for the drug, paclitaxel, in two multi-arm block copolymer embodiments of the invention;

FIG. 6 provides release profiles for the drug, indomethacin, in several polymer compositions;

FIG. 7 provides release profiles for the drug, pivaloxymethyl butyrate, in two multi-arm block copolymer embodiments of the invention;

FIG. 8 provides a release profile for the drug, cyclosporin A, in a multi-arm block copolymer embodiment of the invention;

FIG. 9 provides a release profile for the drug, paclitaxel, in a multi-arm block copolymer embodiment of the invention;

FIG. 10 provides a comparison of the in vivo effect of a conventional Taxol® formulation versus an 8-arm poly (lactide)-mPEG block copolymer/Taxol® formulation of the invention on lung tumor growth; and FIG. 11 is an example of Dynamic Light Scattering (DLS) data.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

I. Definitions

The terms "functional group", "active moiety", "activating group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with functional groups, is intended to include those functional groups that react readily with electrophilic or nucleophilic groups on other molecules, in contrast to those groups that require strong catalysts or highly impractical reaction conditions in order to react (i.e., "non-reactive" or "inert" groups). For example, as would be understood in the art, the term "active ester" would include those esters that react readily with nucleophilic groups such as amines. Exemplary active esters include N-hydroxysuccinimidyl esters or 1-benzotriazolyl esters. Typically, an active ester will react with an amine in aqueous medium in a matter of minutes, whereas certain esters, such as methyl or ethyl esters, require a strong catalyst in order to react with a nucleophilic group.

The term "linkage" or "linker" is used herein to refer to an atom, groups of atoms, or bonds that are normally formed as the result of a chemical reaction. A linker of the invention typically links the connecting moieties, such two polymer segments, via one or more covalent bonds. Hydrolytically stable linkages means that the linkages are substantially stable in water and do not react to any significant degree with water at useful pHs, e.g., under physiological conditions for an extended period of time, perhaps even indefinitely. Hydrolytically unstable or degradable linkages means that the linkages are degradable in water or in aqueous solutions, including for example, blood. Enzymatically unstable or degradable linkages means that the linkage can be degraded by one or more enzymes.

The term "alkyl" refers to hydrocarbon chains typically ranging from about 1 to about 12 carbon atoms in length, and includes straight and branched chains. The hydrocarbon chains may be saturated or unsaturated. The term "substituted alkyl" refers to an alkyl group substituted with one or more non-interfering substituents, such as, but not limited to, C3–C6 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like.

"Alkoxy" refers to an —O—R group, wherein R is alkyl or substituted alkyl, preferably C1–C6 alkyl (e.g., methoxy or ethoxy).

"Aryl" means one or more aromatic rings, each of 5 or 6 core carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents. For substitutions on a phenyl ring, the substituents may be in any orientation (i.e., ortho, meta or para).

"Heteroaryl" is an aryl group containing from one to four N, O, or S atoms(s) or a combination thereof, which heteroaryl group is optionally substituted at carbon or nitrogen atom(s) with C1–6 alkyl, —CF$_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3, 5-triazine); and 6-membered heteroaryls with four heteroatoms.

"Substituted heteroaryl" is heteroaryl having one or more non—interfering groups as substituents.

"Heterocycle" or "heterocyclic" means one or more rings of 5, 6 or 7 atoms with or without unsaturation or aromatic character and at least one ring atom which is not carbon. Preferred heteroatoms include sulfur, oxygen, and nitrogen. Multiple rings may be fused, as in quinoline or benzofuran.

"Substituted heterocycle" is heterocycle having one or more side chains formed from non-interfering substituents.

"Non-interfering substituents" are those groups that yield stable compounds. Suitable non-interfering substituents or radicals include, but are not limited to, halo, C1–C10 alkyl, C2–C10 alkenyl, C2–C10 alkynyl, C1–C10 alkoxy, C7–C12 aralkyl, C7–C12 alkaryl, C3–C10 cycloalkyl, C3–C10 cycloalkenyl, phenyl, substituted phenyl, toluoyl, xylenyl, biphenyl, C2–C12 alkoxyalkyl, C7–C12 alkoxyaryl, C7–C12 aryloxyalkyl, C6–C12 oxyaryl, C1–C6 alkylsulfinyl, C1–C10 alkylsulfonyl, —(CH$_2$)$_m$—O—(C1–C10 alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—(C1–C10 alkyl), —C(O)—(C1–C10 alkyl), C2–C10 thioalkyl, —C(O)O—(C1–C10 alkyl), —OH, —SO$_2$,=S, —COOH, —NR, carbonyl, —C(O)—(C1–C10 alkyl)—CF$_3$, —C(O)—CF$_3$, —C(O)NR$_2$, —(C1–C10 alkyl)—S—(C6–C12 aryl), —C(O)—(C6–C12 aryl), —(CH$_2$)$_m$—O—(CH$_2$)$_m$—O—(C1–C10 alkyl) wherein each m is from 1 to 8, —C(O)NR, —C(S)NR, —SO$_2$NR, —NRC(O)NR, —NRC(S)NR, —NRC(S)NR, salts thereof, and the like. Each R as used herein is H, alkyl or substituted alkyl, aryl or substituted aryl, aralkyl, or alkaryl.

The term "drug", "biologically active molecule", "biologically active moiety" or "biologically active agent", when used herein means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

"Hydrophobic" refers to molecules having a greater solubility in octanol than in water, typically having a much greater solubility in octanol. Conversely, "hydrophilic" refers to molecules having a greater solubility in water than in octanol.

"Poly(hydroxyester)" refers to polymers comprising repeating monomer units of —O—R—C(O)—, wherein R is alkyl, substituted alkyl, aryl, substituted aryl, heteroaryl, substituted heteroaryl, heterocycle, or substituted heterocycle. Exemplary poly(hydroxyesters) include poly(lactide), poly(glycolide), poly(lactide/glycolide) copolymer, poly (butyrolactide), and polycaprolactone.

"Oligomer" refers to short monomer chains comprising 2 to about 10 monomer units.

II. The Multi-Arm Block Copolymer

In one aspect, the present invention provides a multi-arm block copolymer having a hydrophobic core region defined by a central core molecule and hydrophobic polymer arms covalently attached to the central core molecule and an outer hydrophilic region defined by a hydrophilic polymer covalently attached to the hydrophobic polymer arms. Each arm of the multi-arm structure comprises an inner (i.e. closer to the central core molecule) hydrophobic polymer segment and an outer (i.e. further from the central core molecule) hydrophilic polymer segment.

In aqueous solution, it is believed that the multi-arm block copolymer acts as a unimolecular micelle having a central hydrophobic core region bounded by a hydrophilic region. As demonstrated in the experimental section, the multi-arm block copolymers of the invention are capable of increasing the aqueous solubility of hydrophobic biologically active agents or drugs by encapsulating or physically entrapping the hydrophobic drug molecule within the hydrophobic core region of the multi-arm block copolymer structure. Thus, the multi-arm block copolymers are useful as drug delivery vehicles, particularly for hydrophobic drug molecules. "Encapsulation" or "entrapment" is intended to refer to physical confinement of the drug molecule within the hydrophobic region of the copolymer, rather than covalent attachment to the copolymer.

Compared to conventional linear micelle structures, the unimolecular nature of the multi-arm block copolymers of the invention results in less sensitivity to concentration, such that the block copolymers of the invention are less likely to release the entrapped drug molecules at an undesirably rapid rate. The multi-arm block copolymers of the invention are covalently bound molecular units rather than molecular aggregates and, thus, are substantially precluded from disassembly in circulation in the absence of hydrolytically unstable linkages within the polymer segments specifically intended to degrade the copolymer. Further, since chemical modification of the drug molecules is not required to obtain an increase in solubility, the possibility of the copolymer reducing efficacy of the entrapped drug is greatly reduced.

Although not bound by any particular theory, it is believed that the level of hydrophobicity and size of the hydrophobic polymer affect the drug loading and drug release characteristics of the multi-arm block copolymer. In general, it is believed that larger hydrophobic polymer segments and hydrophobic polymer segments formed from polymers having relatively greater degrees of hydrophobicity will result in higher drug loading and slower drug release profiles in solution. Conversely, smaller hydrophobic polymer segments and hydrophobic polymer segments formed from polymers having relatively lower degrees of hydrophobicity will result in reduced drug loading and more rapid drug release.

Further, without being bound by theory, it is believed that the number of arms of the multi-arm block polymer also impacts the drug loading and drug release characteristics of the copolymer. Generally, the presence of fewer copolymer arms results in reduced drug loading. However, the use of a copolymer with a very large number of arms can also reduce drug loading because of the substantial increase in density and concomitant reduction in interstitial space within the hydrophobic core region of the copolymer structure. Generally, the presence of fewer copolymer arms will also result in more rapid drug release. This is attributed, at least in part, to the effect of aggregation of multi-arm block copolymers and entrapment of drug molecules within a hydrophobic region defined by the aggregated copolymers. Aggregation of the multi-arm block copolymers creates hydrophobic regions that are not unimolecular in nature. Instead, a multi-arm block copolymer aggregate behaves in a manner analogous to conventional linear micelles. Reductions in concentration can break up the copolymer aggregate and release a portion of the drug molecules entrapped within the hydrophobic region created by the aggregation. Copolymers with a higher number of arms are less susceptible to the aggregation effect and less likely to have drug release characteristics that depend on concentration. In light of the foregoing, an optimal range for the number of arms of the block copolymer can be determined such that both desirable drug loading and drug release characteristics are obtained for any particular hydrophobic drug. In most embodiments, the number of arms is in the range of 3 to about 25, preferably at least 5, more preferably at least about 8, and most preferably at least about 10.

The hydrophobic and hydrophilic polymer segments are preferably not "hyper-branched" or dendritic in nature, such as the dendrimers described in U.S. Pat. No. 5,830,986, wherein branched compounds are attached in numerous successive layers to a central core. Instead, both polymer segments are preferably substantially linear in nature as depicted in FIG. 1. However, some branching in either polymer segment may be present. For example, a branched poly(ethylene glycol) polymer comprising two polymer backbones attached to lysine linker is used as the hydrophilic polymer in several appended examples.

Although the specific examples of multi-arm block copolymers in the appended experimental section utilize the same block copolymer structure for each copolymer arm, it is possible to utilize different copolymer structures within the same multi-arm structure. In other words, the present invention includes embodiments wherein more than one particular hydrophobic/hydrophilic polymer combination is attached to the same core molecule.

A. The Central Core

The central core molecule is derived from a molecule that provides a number of polymer attachment sites equal to the number of desired copolymer arms. Preferably, the central core molecule of the multi-arm block copolymer structure is the residue of a polyol having at least three hydroxyl groups available for polymer attachment. A "polyol" is a molecule comprising a plurality of available hydroxyl groups. Depending on the desired number of copolymer arms, the polyol will typically comprise 3 to about 25 hydroxyl groups, preferably at least 5, more preferably at least about 8, and most preferably at least about 10. The polyol may include other protected or unprotected functional groups as well without departing from the invention. Although the spacing between hydroxyl groups will vary from polyol to polyol, there are typically 1 to about 20 atoms, such as carbon atoms, between each hydroxyl group, preferably 1 to about 5. As would be understood in the art, by "residue" is meant the portion of the polyol molecule remaining after attachment of the copolymer arms. Preferred polyols include glycerol, reducing sugars such as sorbitol, pentaerythritol, and glycerol oligomers, such as hexaglycerol. As noted in the appended examples, a 21-arm block copolymer can be synthesized using hydroxypropyl-β-cyclodextrin, which has 21 available hydroxyl groups. The particular polyol chosen will depend on the desired number of hydroxyl groups needed for attachment to the copolymer arms.

B. The Hydrophobic Polymer

The particular hydrophobic polymer used in the present invention will depend, at least in part, on the desired drug loading and drug release characteristics, since as explained above, the size and hydrophobicity of the hydrophobic polymer segment will affect those characteristics. The hydrophobic polymer should be generally non-toxic and biocompatible, meaning that the polymer is capable of coexistence with living tissues or organisms without causing harm. In preferred embodiments, the hydrophobic polymer segments comprises a poly(hydroxyester), a poly(alkylene oxide) other than poly(ethylene glycol), such as poly(propylene oxide) (PPO) or poly(butylene oxide) (PBO), or copolymers thereof. Exemplary poly(hydroxyester) polymers include poly(lactide), poly(glycolide), poly(lactide/glycolide) copolymer, poly(butyrolactide) and polycaprolactone. The hydrophobic polymer segment of the block copolymer will typically have a number average molecular weight of about 500 Da to about 100,000 Da, preferably about 10,000 Da to about 40,000 Da. For example, hydrophobic polymer segments having a molecular weight of about 5,000 Da, about 10,000 Da, about 15,000 Da, about 20,000 Da, about 25,000 Da or about 30,000 Da are useful in the present invention.

In addition to being hydrophobic, the poly(hydroxyester) polymers also include one or more hydrolytically or enzymatically degradable linkages, such as ester linkages. Typically, use of these polymers results in the formation of degradable linkages between the central core molecule and the polymer segment, within the polymer segment, between the hydrophobic polymer segment and the hydrophilic polymer segment, or some combination thereof. As used herein, the hydrophobic polymer is said to comprise a degradable linkage if a linkage is located at any of the above-listed locations. The use of a hydrophobic polymer with one or more degradable linkages allows the multi-arm block copolymer to degrade in solution over time, thus increasing renal clearance of the copolymer. In addition, the degradable linkages provide an additional feature of these polymers, i.e., the ability to control the rate of release of the entrapped drug.

C. The Hydrophilic Polymer

The hydrophilic polymer segment may comprise any hydrophilic polymer. As with the hydrophobic polymer, the hydrophilic polymer should be generally non-toxic and biocompatible, meaning that the polymer is capable of coexistence with living tissues or organisms without causing harm. Preferably, poly(ethylene glycol) (PEG) is used as the hydrophilic polymer segment. The term PEG includes poly(ethylene glycol) in any of its linear, branched or multi-arm forms, including alkoxy PEG, bifunctional PEG, forked PEG, branched PEG, pendant PEG, or PEG with degradable linkages therein, to be more fully described below.

In its simplest form, PEG has the formula —CH$_2$CH$_2$O—(CH$_2$CH$_2$O)$_n$—CH$_2$CH$_2$—, where n is from about 10 to about 4000, typically from about 20 to about 500. PEGs having a number average molecular weight of from about 500 Da to about 100,000 Da, preferably about 1,000 Da to about 20,000 Da are particularly useful as the hydrophilic polymer segment. For example, PEG polymer segments having a molecular weight of about 1,000 Da, about 5,000 Da, about 10,000 Da, about 15,000 Da, or about 20,000 Da are useful in the present invention.

In one form useful in the present invention, free or non-bound PEG is a linear polymer terminated at each end with hydroxyl groups:

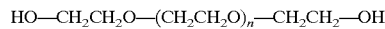

HO—CH$_2$CH$_2$O—(CH$_2$CH$_2$O)$_n$—CH$_2$CH$_2$—OH

The above polymer, alpha-,omega-dihydroxylpoly(ethylene glycol), can be represented in brief form as HO—PEG—OH where it is understood that the —PEG— symbol represents the following structural unit:

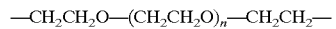

—CH$_2$CH$_2$O—(CH$_2$CH$_2$O)$_n$—CH$_2$CH$_2$— where n typically ranges from about 10 to about 4000.

Another type of PEG useful in forming the conjugates of the invention is methoxy-PEG—OH, or mPEG in brief, in which one terminus is the relatively inert methoxy group, while the other terminus is a hydroxyl group that is subject to ready chemical modification. The structure of mPEG is given below.

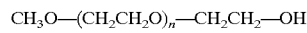

CH$_3$O—(CH$_2$CH$_2$O)$_n$—CH$_2$CH$_2$—OH where n is as described above. The use of hydrophilic polymer segments in the form of mPEG is exemplified in Examples 1 and 4.

Multi-armed or branched PEG molecules, such as those described in U.S. Pat. No. 5,932,462, which is incorporated by reference herein in its entirety, can also be used as the hydrophilic PEG polymer segment. For example, the hydrophilic PEG segment can have the structure:

Formula I

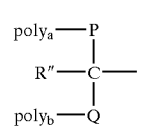

wherein:

Poly$_a$ and poly$_b$ are PEG backbones, such as methoxy poly(ethylene glycol);

R" is a nonreactive moiety, such as H, methyl or a PEG backbone; and

P and Q are nonreactive linkages. In a preferred embodiment, the branched polymer segment comprises methoxy poly(ethylene glycol) disubstituted lysine. Use of such a branched PEG structure is exemplified in Examples 2, 5, and 7.

The PEG polymer may alternatively comprise a forked PEG. An example of a forked PEG is represented by PEG-YCHZ$_2$, where Y is a linking group and Z is an activated terminal group linked to CH by a chain of atoms of defined length. International Application No. PCT/US99/05333, the contents of which are incorporated by reference herein, discloses various forked PEG structures capable of use in the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG segment rather than at the end of the PEG chain. The pendant reactive groups can be attached to the PEG segment directly or through a linking moiety, such as alkylene.

In addition to the above-described forms of PEG, the polymer can also be prepared with one or more weak or degradable linkages in the segment, including any of the above described polymers. For example, PEG can be prepared with ester linkages in the polymer segment that are subject to hydrolysis. As shown below, this hydrolysis results in cleavage of the polymer into fragments of lower molecular weight:

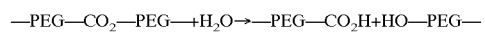

—PEG—CO$_2$—PEG—+H$_2$O→—PEG—CO$_2$H+HO—PEG—

Similarly, the PEG polymer can be covalently attached to the hydrophobic polymer segment or other molecules through a weak or degradable linkage moiety.

Other hydrolytically degradable linkages, useful as either a degradable linkage within a polymer segment or as a degradable linkage connecting the PEG polymer to other molecules include carbonate linkages; imine linkages resulting, for example, from reaction of an amine and an aldehyde (see, e.g., Ouchi et al., Polymer Preprints, 38(1):582–3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those skilled in the art that the term poly(ethylene glycol) or PEG represents or includes all the above forms of PEG.

In some embodiments, it may be desirable to covalently attach a targeting moiety or drug molecule to the hydrophilic polymer segment. As used herein, "targeting moiety" includes any chemical moiety capable of binding to, or otherwise exhibiting an affinity for, a particular type of tissue or component thereof. The addition of a targeting moiety to the copolymer structure can direct the copolymer to particular sites within the body for targeted release of the physically entrapped drug. For example, certain moieties are known to exhibit an affinity for hydroxyapatite surfaces (i.e. calcium phosphate), such as bone. Exemplary hydroxyapatite-targeting moieties include tetracycline, calcein, bisphosphonates, such as 4-amino-1-hydroxybutane-1,1-diphosphonic acid, ditetrabutylammonium salt (AHBDP) or derivatives thereof, polyaspartic acid, polyglutamic acid, and aminophosphosugars. Additional targeting moieties include proteins, antibodies, antibody fragments, peptides, carbohydrates, lipids, oligonucleotides, DNA, RNA, or small molecules having a molecular weight less than 2000 Daltons.

The PEG polymer segment may further include one or more capping groups covalently attached to the PEG molecule, such as at a terminus of the PEG segment distal from the point of attachment to the hydrophobic polymer. The capping group can be a relatively inert group, such as an alkoxy group (e.g. methoxy or ethoxy). Alternatively, the capping group can be a reactive functional group, such as a functional group capable of reacting with a targeting moiety or drug molecule so that such molecules can be attached to the PEG polymer as described above. Exemplary functional groups, optionally in protected form, include hydroxyl, protected hydroxyl, active ester (e.g. N-hydroxysuccinimidyl, 1-benzotriazolyl, p-nitrophenyl, or imidazolyl esters), active carbonate (e.g. N-hydroxysuccinimidyl, 1-benzotriazolyl, p-nitrophenyl, or imidazolyl carbonate), acetal, aldehyde, aldehyde hydrates, alkyl or aryl sulfonate, halide, disulfide derivatives such as o-pyridyl disulfidyl, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, or tresylate.

As would be understood in the art, the term "protected" refers to the presence of a protecting group or moiety that prevents reaction of the chemically reactive functional group under certain reaction conditions. The protecting group will vary depending on the type of chemically reactive group being protected and the reaction conditions employed. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the invention, see for example, Greene, T. W., et al., *PROTECTIVE GROUPS IN ORGANIC SYNTHESIS*, 2nd ed., John Wiley & Sons, New York, N.Y. (1991).

Specific examples of functional groups for the hydrophilic polymer include N-succinimidyl carbonate (see e.g., U.S. Pat. Nos. 5,281,698, 5,468,478), amine (see, e.g., Buckmann et al. Makromol.Chem. 182:1379 (1981), Zaplipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170–181, Harris & Zaplipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Macrolol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985; and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824, 784, U.S. Pat. 5,252,714); maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). All of the above references are incorporated herein by reference.

D. Exemplary Multi-Arm Block Copolymer Structures

More specific structural embodiments of the block copolymers of the invention will now be described. The specific structures shown below are presented as exemplary structures only, and are not intended to limit the scope of the invention.

In one embodiment, a block copolymer of the invention is represented by Formula II:

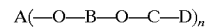

A(—O—B—O—C—D)$_n$ wherein:
A is a central core molecule as described above, such as a residue of a polyol having at least three hydroxyl groups,
O is oxygen,
B is a hydrophobic polymer segment as described above,
C is a hydrophilic polymer segment as described above,
D is a capping group as described above, and
n is 3 to about 25, preferably at least about 5, more preferably at least about 8, and most preferably at least about 10.

In a further embodiment, the block copolymer has the following structure represented by Formula III:

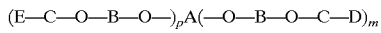

wherein:

A, O, B, C are as described above,

D is an alkoxy or hydroxy group, p is at least 1, the sum of m and p is from 3 to about 25, and E is a functional group as described above.

In a third embodiment, the copolymer has the following structure represented by Formula IV:

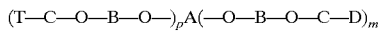

wherein:

A, O, B, C are as described above,

D is a capping group, p is at least 1, the sum of m and p is from 3 to about 25, and T is a targeting moiety or drug moiety as described above, such as a bisphosphonate.

Regarding Formulas III and IV above, in one embodiment, p is 1 to about 5, preferably 1 to about 3, and the sum of m and p is about 6 to about 21, preferably about 8 to about 15.

Formula V below is an exemplary 8-arm PPO—PEG block copolymer made in accordance with the invention:

Formula V

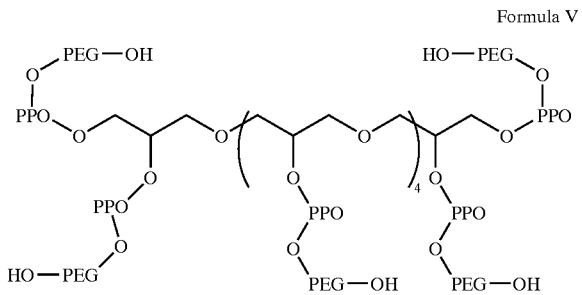

Formula VI below is an exemplary 8-arm degradable poly(lactide)-poly(ethylene glycol) (PLA—PEG) block copolymer of the invention:

Formula VI

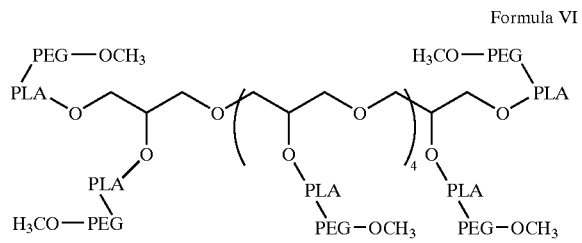

E. The Hydrophobic Drug

The hydrophobic biologically active moiety or drug may be any biologically active hydrophobic compound that would benefit from increased aqueous solubility. The entrapped or encapsulated drug may be utilized per se or in the form of a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulphonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

Examples of hydrophobic drug molecules that may be encapsulated within the multi-arm block copolymers of the invention include, but are not limited to, abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allylsulfide, alprazolam, aluminum bis(acetylsalicylate), ambucetamide, aminochlothenoxazin, aminoglutethimide, amyl. chloride, androstenediol, anethole trithone, anilazine, anthralin, Antimycin A, aplasmomycin, arsenoacetic acid, asiaticoside, astemizole, aurodox, aurothioglycanide, 8-azaguanine, azobenzene, baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bomyl, bromoisovalerate, bomyl chloride, bomyl isovalerate, bornyl salicylate, brodifacoum, bromethalin, broxyquinoline, bufexamac, butamirate, butethal, buthiobate, butylated hydroxyanisole, butylated hydroxytoluene, calcium iodostearate, calcium saccharate, calcium stearate, capobenic acid, captan, carbamazepine, carbocloral, carbophenothin, carboquone, carotene, carvacrol, cephaeline, cephalin, chaulmoogric acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofaziminc, clofibrate, cloflucarban, clonitrate, clopidol, clorindione, cloxazolam, coroxon, corticosterone, coumachlor, coumaphos, coumithoate cresyl acetate, crimidine, crufomate, cuprobam, cyamemazine, cyclandelate, cyclarbamate cymarin, cyclosporin A, cypermethril, dapsone, defosfamide, deltamethrin, deoxycorticocosterone acetate, desoximetasone, dextromoramide, diacetazoto, dialifor, diathymosulfone, decapthon, dichlofluani, dichlorophen, dichlorphenamide, dicofol, dicryl, dicumarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicotinamide, 3,4-di-[1-methyl 6-nitro-3-indolyl]-1H-pyrrole-2,5-dione (MNIPD), dipyrocetyl, disulfamide, dithianone, doxenitoin, drazoxolon, durapatite, edifenphos, emodin, enfenamic acid, erbon, ergocominine, erythrityl tetranitrate, erythromycin stearate, estriol, ethaverine, ethisterone, ethyl biscoumacetate, ethylhydrocupreine, ethyl menthane carboxamide, eugenol, euprocin, exalamide, febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, flurothyl, flutazolam, fumagillin, 5-furftiryl-5-isopropylbarbituric acid, fusaftmgine; glafenine, glucagon, glutethimide, glybuthiazole, griseofulvin, guaiacol carbonate, guaiacol phosphate; halcinonide, hematoporphyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1,3-dione, josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenytoin, meprylcaine, mestanolone, mestranol, mesulfen, metergoline, methallatal, methandriol, methaqualone, methylcholanthrene, methylphenidate, 17-methyltestosterone, metipranolol, minaprine, myoral, naftalofos, naftopidil, naphthalene, 2-naphthyl lactate, 2-(2-naphthyloxy)ethanol, naphthyl salicylate, naproxen, nealbarbital, nemadectin, niclosamide, nicoclonate, nicomorphine, nifuroquine, nifuroxazide, nitracrine, nitromersol, nogalamycin, nordazepam, norethandrolone, norgestrienone, octaverine, oleandrin, oleic acid, oxazepam, oxazolam, oxeladin, oxwthazaine, oxycodone, oxymesterone, oxyphenistan acetate, paclitaxel, paraherquamide, parathion, pemoline, pentaerythritol tetranitrate, pentylphenol, perphenazine, phencarbamide, pheniramine, 2-phenyl-6-chlorophenol, phenthnethylbarbituric acid, phenytoin, phosalone, O-phthalylsulfathiazole, phylloquinone, picadex, pifarnine, piketopfen, piprozolin, pirozadil, pivaloyloxymethyl butyrate, plafibride, plaunotol, polaprezinc, polythiazide, probenecid, progesterone, promegestone, propanidid, propargite, propham, proquazone, protionamide, pyrimethamine, pyrimithate, pyrvinium pamoate, quercetin, quinbolone, quizalofo-ethyl, rafoxanide, rescinnamine, rociverine, ronnel, salen, scarlet red, siccanin, simazine, simetride, simvastatin, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thioctic acid, thioquinox, thioridazine, thiram, thymyl N-isoamylcarbamate, tioxidazole, tioxolone, tocopherol, tolciclate, tolnaftate, triclosan, triflusal, triparanol, ursolic acid, valinomycin, verapamil, vinblastine, vitamin A, vitamin D, vitamin E, xenbucin, xylazine, zaltoprofen, and zearalenone.

III. Pharmaceutical Compositions Comprising the Multi-Arm Block Copolymer

In another aspect, the invention provides pharmaceutical formulations or compositions, both for veterinary and for human medical use, comprising a multi-arm block copolymer as described above and at least one biologically active agent entrapped within the hydrophobic core region of the multi-arm block copolymer. As noted previously, incorporation of a hydrophobic drug into the block copolymer structure of the invention increases the aqueous solubility of the drug, which can enhance the circulating residence time of the drug upon administration to a mammal.

The pharmaceutical formulation may include one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions of the invention may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), and in "Handbook of Pharmaceutical Excipients", Third Ed., Ed. A. H. Kibbe, Pharmaceutical Press, 2000.

The block copolymers of the invention may be formulated in compositions including those suitable for oral, buccal, rectal, topical, nasal, ophthalmic, or parenteral (including intraperitoneal, intravenous, subcutaneous, or intramuscular injection) administration. The block copolymers may also be used in formulations suitable for inhalation. The compositions may conveniently be presented in unit dosage form and may be prepared by any of the methods well known in the art of pharmacy. All methods include the step of bringing the block copolymer with drug entrapped therein into association with a carrier that constitutes one or more accessory ingredients. In general, the compositions are prepared by bringing the block copolymer/drug formulation into association with a liquid carrier to form a solution or a suspension, or alternatively, bringing the block copolymer/drug formulation into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

The amount of the biologically active agent or drug in the formulation will vary depending upon the specific drug employed, its molecular weight, and other factors such as dosage form, target patient population, and other considerations, and will generally be readily determined by one skilled in the art. The amount of biologically active agent in the copolymer formulation will be that amount necessary to deliver a therapeutically effective amount of the drug to a patient in need thereof to achieve at least one of the therapeutic effects associated with the drug. In practice, this will vary widely depending upon the particular drug, its activity, the severity of the condition to be treated, the patient population, the stability of the formulation, and the like. Compositions will generally contain anywhere from about 1% by weight to about 30% by weight drug, typically from about 2% to about 20% by weight drug, and more typically from about 3% to about 15% by weight drug, and will also depend upon the relative amounts of excipients/ additives contained in the composition. More specifically, the composition will typically contain at least about one of the following percentages of the entrapped drug: 0.5%, 1%, 2%, 3%, 4%, 5%, 6%, 7%, 8%, 9%, 10%, 12%, 14%, 16%, 18%, 20%, or more by weight.

IV. Methods of Making the Block Copolymer

The multi-arm block copolymers of the invention can be prepared by simply covalently attaching a preformed hydrophobic polymer segment to the core molecule followed by covalently attaching a preformed hydrophilic polymer segment to the hydrophobic polymer segment. Alternatively, one or more of the polymer segments can be prepared by directly polymerizing monomer units of the polymer using, for example, a ring-opening polymerization technique.

For example, in order to synthesize a poly(propylene oxide)-poly(ethylene glycol) copolymer (PPO—PEG) on a polyol core, the propylene oxide monomers can be directly polymerized onto the polyol core by base-initiated ring-opening polymerization in a suitable solvent. Suitable bases include potassium naphthalenide, sodium hydride, sodium or potassium alkoxides, or other strong bases. Suitable solvents include tetrahydrofuran, dioxane, or toluene. In a second step, the product of the first reaction is reacted with monomer units of ethylene oxide using a base and solvent as described for the first reaction. The molecular weight of the PPO polymer formed in the first step is controlled by the molar ratio of the propylene oxide to that of the polyol. The molecular weight of the PEG polymer formed in the second step is controlled by the molar ratio of the ethylene oxide to that of the PPO polymer formed in the first step.

In those embodiments utilizing a poly(hydroxyester) hydrophobic polymer segment and a PEG hydrophilic polymer segment, it is preferable to directly polymerize the hydroxyester monomer onto the core molecule (e.g. a polyol) to create the poly(hydroxyester) portion of the copolymer, followed by covalent attachment of the PEG polymer to the distal terminus of the poly(hydroxyester) segment.

V. Methods of Loading the Drug into the Multi-Arm Block Copolymer

There are several methods for entrapping a biologically active agent or drug within the hydrophobic region of the block copolymers of the invention. In a first method, the hydrophobic drug and the copolymer are co-dissolved in an organic solvent and then dried to form a solid product. The solid product is redissolved in aqueous solution and filtered to remove insoluble particles prior to use. In a second method, the hydrophobic drug is suspended in an aqueous solution of the copolymer and subjected to ultrasonication for several hours in order to intimately contact the drug molecules and the hydrophobic cores of the copolymer structures. The solution is then filtered to remove insoluble particles. In a third method, the hydrophobic drug and the polymer are mixed in solid form and heated to about 60° C. to form a melt. The melt is stirred for several hours to encourage intimate mixing of the drug and copolymer. After cooling to room temperature, the formulation is ready for immediate use or storage.

VI. Method of Using the Multi-Arm Block Copolymers

As noted above, the multi-arm block copolymers of the invention can be used to solubilize hydrophobic drug molecules in aqueous solution. As a result, the copolymer structures of the invention may be used as drug delivery vehicles by entrapping the hydrophobic drug within the hydrophobic region of the copolymer and administering a therapeutically effective amount of the multi-arm block copolymer with the biologically active agent entrapped therein to a mammal.

The block copolymers of the invention can be used as drug delivery vehicles for any condition responsive to a hydrophobic drug molecule capable of entrapment within the copolymer structure. Thus, the block copolymers of the invention can be used in pharmaceutical formulations useful for treating any condition responsive to a hydrophobic drug in mammals, including humans. A preferred condition for treatment is cancer. The method of treatment comprises administering to the mammal a therapeutically effective amount of a composition or formulation containing the multi-arm block copolymer with a hydrophobic drug encapsulated therein as described above. The therapeutically effective dosage amount of any specific formulation will vary somewhat from drug to drug, patient to patient, and will depend upon factors such as the condition of the patient, the loading capacity of the block copolymer, and the route of delivery. As a general proposition, a dosage from about 0.5 to about 20 mg/kg body weight, preferably from about 1.0 to about 5.0 mg/kg, will have therapeutic efficacy. When administered conjointly with other pharmaceutically active agents, even less of the block copolymer/hydrophilic drug composition may be therapeutically effective.

The block copolymer/hydrophilic drug composition may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, or by inhalation.

VII. Experimental

The following examples are given to illustrate the invention, but should not be considered in limitation of the invention. Unless otherwise indicated, all PEG reagents are available from Shearwater Corporation of Huntsville, Ala. All NMR data was generated by a 300 MHz NMR spectrometer manufactured by Bruker.

Materials

Four 8-arm block copolymers were prepared. In each case, the poly(propylene oxide) (PPO) segments of the copolymers were covalently bonded to a hexaglycerol core through ether linkages and the poly(ethylene glycol) (PEG) moiety was covalently bound to the distal terminus of each PPO segment. Copolymer PPO—PEG of nominal molecular weight 8500 Da was prepared with a 5300 Da PPO block and a 3200 Da PEG block. Copolymer PPO—PEG 18000 (18000 Da molecular weight) was prepared with a 5300 Da PPO block and a 12,700 Da PEG block. Copolymer PPO—PEG 16000 was prepared with a 9500 Da PPO block and a 6500 Da PEG block. Copolymer PPO—PEG 22000 was prepared with a 9500 Da PPO block and a 12,000 Da PEG block. It should be understood that these molecular weights are an average, nominal, molecular weight for polymers having a range of molecular weights. The general structure of a PPO—PEG copolymer of this type is given above as Formula V.

Additionally, a series of degradable multi-arm copolymers were synthesized, in which degradable poly (hydroxyesters) were used as hydrophobic segments. These copolymers include 8-arm polylactide mPEG$_{5kDa}$ (8-arm PLA—mPEG$_{5kDa}$), 8-arm polylactide PEG2$_{6kDa}$ (8-arm-PLA—PEG2$_{6kDa}$), 8-arm polycaprolactone mPEG$_{5kDa}$ (8-arm-PCL—mPEG$_{5kDa}$), 8-arm polycaprolactone PEG2$_{6kDa}$ (8-arm-PCL—PEG2$_{6kDa}$), PEG2 attached to hydroxypropyl-β-cyclodextrin polycaprolactone (BCD—PCL—PEG2$_{6kDa}$). All of the 8-arm degradable copolymers were made using a hexaglycerol core. The general structure of an 8-arm polylactide mPEG is given above as Formula VI. The 21-arm BCD—PCL—PEG2$_{6kDa}$ copolymer comprises a hydroxypropyl-β-cyclodextrin core. As used herein, PEG2 refers to a branched PEG structure comprising two PEG backbones attached to a lysine linker, as described in U.S. Pat. No. 5,932,462. Examples 1–7 illustrate methods of synthesizing multi-arm poly(hydroxyester)-PEG copolymers.

For comparative purposes, the following additional materials were tested: Tetronic® 1037, a four arm PPO—PEG copolymer having nitrogen branching points available from BASF Corp. (Mount Olive, N.J.); two multi-arm PEG molecules available from NOF (Tokyo, Japan), a 4-arm copolymer comprising a pentaerythritol core and an 8-arm copolymer comprising a hexaglycerol core; and Tween® 80, a polyoxyethylene sorbitan monooleate surfactant obtained from Aldrich (Milwaukee, Wis.). Physical data for all tested materials is listed in Table 1 below.

TABLE 1

Physical data of the materials used in the experiments

|  | Polymer | Mw (Da) | Wt. % of PEG | # of arm |
|---|---|---|---|---|
| Non-degradable | PPO-PEG 6030 | 8500 | 36 | 8 |
|  | PPO-PEG 6070 | 18000 | 68 | 8 |
|  | PPO-PEG 10037 | 16000 | 38 | 8 |
|  | PPO-PEG 10050 | 22000 | 54.5 | 8 |
|  | Tetronic ® 1307 | 18000 | 70 | 4 |
|  | PEG10 kDa | 10000 | 100 | 4 |
|  | PEG10 kDa | 10000 | 100 | 8 |
|  | Tween 80 | 1310 | 67 | N/A |
| Degradable | PLA-mPEG$_{5kDa}$ | 56000 | 71 | 8 |
|  | PLA-PEG2$_{6kDa}$ | 64000 | 75 | 8 |
|  | PCL-mPEG$_{5kDa}$ | 56000 | 71 | 8 |
|  | PCL-PEG2$_{6kDa}$ | 64000 | 75 | 8 |
|  | BCD-PCL-PEG2$_{6kDa}$ | 168000 | 75 | 21 |

The following biologically active agents were used in the formulation and release studies detailed below: 3,4-di-[1-methyl 6-nitro-3-indolyl]-1H-pyrrole-2,5-dione (MNIPD) (available from F. Hoffiann-La Roche Ltd, Basel, Switzerland), simvastatin (available from Merck & Co., Inc., Whitehouse Station, N.J., USA), indomethacin (available from Sigma, St. Louis, Mo., USA), pivaloyloxymethyl butyrate (available from Titan Pharmaceuticals, Inc., San Francisco, Calif., USA), cyclosporin A (available from Fluka, Milwaukee, Wis., USA), and paclitaxel (available from LKT laboratories, Inc., St. Paul, Minn., USA).

Drug Loading Methods

Three methods were used to load a hydrophobic drug into the multi-arm block copolymer formulations. Method I utilized an organic solvent. Method II utilized an aqueous solution. Method III was performed in the absence of a solvent.

Method I: The hydrophobic drug and the copolymer were co-dissolved in methylene chloride. The solution was air-dried overnight and then dried under vacuum. The resulting solid was either stored at −20° C. for future use after thawing, dissolving in buffer, and filtering, or it was dissolved immediately in a buffer, filtered to remove insoluble particles and the filtrate frozen and stored at −20° C.

Method II: The hydrophobic drug was suspended in a buffered polymer solution. The suspension was subjected to ultrasonication for about three hours, and then filtered through a 0.2 μm syringe filter. The filtrate was frozen and stored at −20° C.

Method III: The hydrophobic drug and the polymer were placed in a capped vial under argon and heated to 60° C. to form a melt. The melt was stirred for two hours using a magnetic stirrer. After cooling to room temperature, the formulation was ready for immediate use or storage for future use.

EXAMPLE 1

Preparation of 8-arm Polylactide-mPEG$_{5kDa}$ (8-arm-PLA—mPEG$_{5kDa}$)

In a 250 mL three neck round bottom flask, hexaglycerol (4.307 gm, 0.008 moles (Sakamoto Yakuhin Kogyo Co., Ltd., Osaka, Japan) was heated at 100° C. for one hour under vacuum (1 mmHg). The contents were cooled to ambient temperature and placed under argon. DL-lactide (160 gm, 1.110 moles (Purasorb, Purac, Holland) was added and the flask flushed with argon then heated at 150° C. Stannous 2-ethyhexaneoate (94.6 mg, 2.22×10$^{-4}$ moles) was added and the mixture heated under argon at 170° C. for twenty-four hours. The mixture was cooled to 160° C. and stirred under vacuum (less than 1 mm Hg) for three hours. After cooling to room temperature the mixture was dissolved in dichloromethane (900 mL). The solution was concentrated to near dryness at reduced pressure and poured into hexanes (1500 mL) with stirring to precipitate. The supernatant was decanted and the residue dried under vacuum. NMR (CDCl$_3$): δ 5.16 (m, —OCH(—CH$_3$)CO—), 1.57 (d, ill resolved, —OCH(—CH$_3$)CO—).

In a round-bottom flask, 8-arm PLA prepared from above (2 grams), mPEG$_{5k}$-CM (5 grams), 1-hydroxybenzotriazole (HOBT, 65 mg), 4-(dimethylamino)pyridine (DMAP, 120 mg) and dicyclohexylcarbodiimide (DCC, 288 mg) were mixed with 40 ml of anhydrous methylene chloride. The mixture was stirred at room temperature overnight, the insoluble solid was removed by filtration, and the solvent was evaporated under reduced pressure. The residue was added to 100 ml of ether and the resulting precipitate was collected by filtration and dried under vacuum. Yield: 5.5 g (78%). $^1$H NMR(DMSO-d$_6$): δ 3.5 (br m, PEG), 4.20 (s, —PEG—OCH2COO—PLA), 5.16 (m, —OCH(—CH$_3$) CO—, 1.45 (d, ill resolved, —OCH(—CH$_3$)CO—).

EXAMPLE 2

Preparation of 8-arm Polylactide PEG2$_{6kDa}$ (8-arm-PLA—PEG2$_{6kDa}$)

8-arm-polylactide (8-arm-PLA) (3.00 g, Mw~20 kDa), branched PEG carboxylic acid (PEG2—COOH, 6kDa, 7 g), DMAP (120 mg), HOBT (105 mg) and DCC (440 mg) were dissolved in methylene chloride (50 ml). The reaction was stirred at room temperature for about 72 hours. The solvent was then removed under vacuum, and 35 ml of 1,4 dioxane was added to the syrup. After filtering, the filtrate was added to 200 ml of diethyl ether. The precipitate was collected by filtration, washed with isopropyl alcohol (IPA) and ether, and then dried overnight under vacuum. Yield: 9.4 g. $^1$H NMR(DMSO-d$_6$): δ 3.5 (br m, PEG), 1.45 (d, —OCCH(C H$_3$)O—), 5.165 (m, OCCH(CH$_3$)O—), 4.03 (t, mPEGOCH$_2$CH$_2$OCONH—).

Example 3

Preparation of 8-arm ε-Polycaprolactone (8-arm PCL)

Hexaglycerol (2.156 g) was dried by heating at 100° C. for 16 hours under vacuum. Five ml of N, N-dimethyl formamide was added and the mixture heated under argon to 80° C. To the resulting mixture was added 80 g (74 ml) of ε-caprolactone (Aldrich) and stannus ethyl hexaneoate (48 mg). The mixture was heated to 110° C. for ~72 h. The flask was cooled and unreacted reagent and solvent were removed under vacuum. Yield: ~80 g. $^1$H NMR(DMSO-d$_6$): δ 1.23 (br m, —OCCH$_2$CH$_2$CH$_2$CH$_2$CH$_2$O—), 1.52 (m, —OCCH$_2$CH$_2$CH$_2$CH$_2$CH$_2$O—), 2.26 (t, —OCC H$_2$CH$_2$CH$_2$CH$_2$O—), 3.98 (t, —OCCH$_2$CH$_2$CH$_2$CH$_2$CH2O—). The molecular weight of the 8-arm-PCL was estimated as 16000 Dalton by NMR and GPC.

EXAMPLE 4

Preparation of 8-arm Polycaprolactone mPEG$_{5kDa}$ (8-arm-PCL—mPEG$_{5kDa}$)

8-arm-PCL from Example 3(1.00 g), carboxymethyl mPEG$_{5kDa}$ (2.10 g), DMAP (60 mg), HOBT (35 mg) and DCC (140 mg) were dissolved in methylene chloride (30 ml). The reaction was stirred at room temperature for 46 hours. The solvent was then removed under vacuum, and 15 ml of 1,4 dioxane was added to the syrup. After filtering, the filtrate was concentrated by removing excess 1,4 dioxane under vacuum. The product was precipitated with 200 ml of diethyl ether, stirred for 5 minutes, and collected by filtration. The product was dried overnight under vacuum. Yield: 2.6 g. $^1$H NMR(DMSO-d$_6$): δ 3.5 (br m, PEG), 4.20 (s, —PEG—OCH$_2$COO—PCL), 1.28 (br m, —OCCH$_2$CH$_2$C H$_2$CH$_2$CH$_2$O—), 1.55 (m, —OCCH$_2$CH$_2$C H$_2$CH$_2$O—), 2.26 (t, —OCCH$_2$CH$_2$CH$_2$CH$_2$CH$_2$O—), 3.99 (t, —OCCH$_2$CH$_2$CH$_2$CH$_2$CH$_2$O—).

EXAMPLE 5

Preparation of 8-arm Polycaprolactone PEG2$_{6kDa}$ (8-arm-PCL—PEG2$_{6kDa}$)

8-arm-PCL (1.00 g), branched PEG carboxylic acid (PEG2$_{6kDa}$—COOH, 2.52 g), DMAP (60 mg), HOBT (35 mg) and DCC (140 mg) were dissolved in methylene chloride (30 ml). The reaction was stirred at room temperature for about 72 hours. The solvent was then removed under vacuum, and 15 ml of 1,4 dioxane was added to the syrup. After filtering with celite, the filtrate was concentrated by removing excess 1,4 dioxane under vacuum. The product was precipitated with 200 ml of diethyl ether, stirred for 5 minutes, collected by filtration, and dried overnight under vacuum. Yield: 3.1 g $^1$H NMR(DMSO-d$_6$): δ 3.5 (br m, PEG), 1.28 (br m, —OCCH$_2$CH$_2$CH$_2$CH$_2$CH$_2$O—), 1.55 (m, —OCCH$_2$CH$_2$CH$_2$CH$_2$CH$_2$O—), 2.26 (t, —OCC H$_2$CH$_2$CH$_2$CH$_2$O—), 3.99 (t, —OCCH$_2$CH$_2$CH$_2$CH$_2$C H$_2$O—).

EXAMPLE 6

Preparation of Polycaprolactone Initiated with Hydroxypropyl-β-cyclodextrin (BCD—PCL)

Hydroxypropyl-β-cyclodextrin (BCD; 100 substitution) was purchased from Aldrich and used as received. ε-Caprolactone (CL; Aldrich) was purified by dehydration with CaH$_2$ and distillation under vacuum. The purified product was stored under N$_2$ atmosphere at −20° C. until use. Stannous 2-ethyhexaneoate (SnOct; Aldrich) and all other reagents were used as received.

Hydroxypropyl-β-cyclodextrin (BCD, 1.45 gram, 1 mmol) was vacuum-dried in a round-bottomed flask at 100° C. for 1 hour and purged with dry N$_2$. Purified ε-caprolactone (42 gram, 0.368 mol) was added to the flask using a syringe. Thirty-two milligrams of stannous 2-ethyhexaneoate (SnOct, Aldrich) was added, and the mixture stirred for 24 hours. The mixture of reagents became viscous without significant change in color. While the mixture was cooled, tetrahydrofuran (100 ml) was added. The polymer was precipitated by addition of about 2 L of isopropanol (IPA). The precipitate was collected by filtration and redissolved in benzene and freeze-dried for 2 days. Yield: 37 g (86%).

EXAMPLE 7

Preparation of PEG2 attached to BCD—PCL (BCD—PCL—PEG2$_{6kDa}$)

One gram of BCD—PCL was mixed with 3.8 g (0.025 mmol) of PEG2-carboxylic acid (MW6,000), 0.866 g of dicyclohexyl carbodiimide (4.2 mmol), 0.122 g of 4-dimethylaminopyridine (1.0 mmol) and 0.068 g of hydroxybenzotriazole (0.5 mmol) in 20 ml of 1,2-dichloroethane (or dichloromethane), and stirred for 48 hours. The solvent was removed under vacuum, and the remaining gummy material was dissolved in 40 ml of 1,4-dioxane. The undissolved material was removed by filtration and the solution was added to 400 ml of diethyl-ether. The precipitate was filtered and dried under vacuum for 48 h. Yield: 4.2 gram (88%).

EXAMPLE 8

Synthesis of Bisphosphonate Derivative of Multi-Arm PPO—PEG 8 arm PPO—PEG(18KDa)(succinimidyl carbonate)$_8$ 8 arm PPO—PEG (18KDa)(15.0 g,~0.83 mmol) in acetonitrile (200 mL) was treated with disuccinimidyl carbonate (DSC) (1.9 g, 7.4 mmol) and pyridine (0.70 ml). The reaction was stirred overnight at room temperature under an argon atmosphere. The reaction was concentrated to dryness and the residue was dissolved in dichloromethane (~200 ml). The clear solution was washed with a 10% solution of sodium phosphate, sodium chloride (2×200 ml). The organic layer was dried (Na$_2$SO$_4$), filtered, and the solvent was removed to afford 8 arm PPO—PEG (18 KDa)-(α-succinimidyl carbonate)$_8$ (15.0 g,~100%).

8 arm PPO—PEG(18 KDa)(AHBDP)$_5$ 8 arm PPO—PEG (18KDa)-(α-succinimidyl carbonate)$_8$ (10.0 g,~0.55 mmol) and 4-amino-1-hydroxybutane-1,1-diphosphonic acid, ditetrabutylammonium salt (AHBDP) (2.96 g, 3.76 mmol) were dissolved in acetonitrile (200 ml) and treated with triethylamine (0.8 ml, 5.74 mmol). The clear, colorless solution was stirred overnight under and argon atmosphere. The solution was concentrated to dryness, the residual gum dissolved in water (100 mL), and the pH was adjusted to 11. The basic solution was stirred at room temperature for 2 h. The solution was then adjusted pH 7.0 with HCl and passed through an IR 120 column (75 ml). The water was removed in vacuo at ca. 50° C. to afford the product as a gum. Further drying in vacuo followed by trituration with CH$_2$Cl$_2$ with Et$_2$O afforded the product as a waxy solid (4.5 g). $^1$H NMR (dmso-d$_6$, 300 MHz) δ 1.04 (d, 280H, OCH(CH$_3$)CH$_2$), 1.59–1.76 (m, 12.5H, OCONHCH$_2$CH$_2$CH$_2$), 1.76–1.94 (m, 12.4H, OCONHCH$_2$CH$_2$CH$_2$), 2.88–2.99 (m, 12.9H, OCONHCH$_2$CH$_2$CH$_2$), 3.51 (bs, 1191H, PEG backbone), 4.03 (t, 13H, J 4.4 Hz, CH$_2$CH$_2$OCONH), 7.16 (t, 5.0H, J 5.1 Hz, CH$_2$CH$_2$OCONH).

Example 8 illustrates a method of synthesizing a multi-arm copolymer including a targeting moiety attached to a distal end of the outer PEG polymer.

EXAMPLE 9

Preparation of Cyclosporin A-Loaded 8-Arm-PCL—PEG2$_{6kDa}$

In a glass vial, 6 mg of cyclosporin A and 60 milligram of 8-arm-PCL—PEG2$_{6kDa}$ (drug/polymer weight ratio 1/10) were dissolved in 1 ml of methylene chloride. The solution was dried under argon. The dried solid was heated at 55° C. for two hours under argon. The melt was then cooled to room temperature, placed under vacuum overnight, and reduced to small particles. To the particles was added 1 ml of phosphate buffer (0.1 M, pH 7.0), and the resulting mixture was filtered through 0.2 μm syringe filter. Cyclosporin A concentration was 5.5 mg/ml by HPLC.

EXAMPLE 10

Preparation of Paclitaxel-Loaded 8-Arm-PCL—PEG2$_{6kDa}$

Paclitaxel (6 mg) and 8-arm-PCL—PEG2$_{6kDa}$ (60 mg) (drug/polymer weight ratio 1/10) were dissolved in 1 ml of methylene chloride. The solution was dried under argon. The dried solid was heated at 55° C. for two hours under argon. The melt was then cooled to room temperature and placed under vacuum overnight, and reduced to small particles. To the particles was added 1 ml of phosphate buffer (0.1 M, pH 7.0). The resulting mixture was filtered through 0.2 μm syringe filter. Paclitaxel concentration was above 4.5 mg/ml by HPLC.

EXAMPLE 11

Solubility of Drugs in PPO—PEG Multi-Arm Block Copolymers

For several drug molecules, 50 mg of PPO—PEG block copolymer 10050/drug formulation with 10 wt. % of drug loading was dissolved in 1 ml of phosphate buffer (0.1 M, pH 7.4). After two hours of mixing, the mixture was filtered through 0.2 μm syringe filter. The drug concentration in the filtrate was determined by HPLC or UV using a standard curve. The results are listed in Table 2. As noted in Table 2, in each case, incorporation of the drug into the multi-arm PPO—PEG block copolymer greatly increased the solubility of the drug in buffer solution.

TABLE 2

Solubility of Drug in 50 mg of the Multi-Arm PPO-PEG Block Copolymer (phosphate buffer, 0.1 M, pH 7.4).

| Drug | MNIPD | Simvastatin | Indomethacin | Paclitaxel | Pivaloyloxymethyl butyrate |
|---|---|---|---|---|---|
| Solubility of Drug in Plain Buffer | <0.5 μg/ml | <1 μg/ml | 88 μg/ml | <1 μg/ml | — |
| Solubility of Drug in Copolymer/Drug Formulation | 2.6 mg/ml | 4 mg/ml | 4 mg/ml | 2 mg/ml | 12 mg/ml |
| Solubility of Formulation Relative to Solubility in Buffer | ~5,000 | ~4,000 | ~45 | ~2,000 | — |

EXAMPLE 12

Degradation Studies of Degradable Multi-Arm Block Copolymers

Each of the multi-arm PEG block copolymers having degradable hydrophobic segments was dissolved in either phosphate buffer (0.1 M, pH 7.0) or rat serum to a final concentration of 1–4 wt. %. The solution was placed in an incubator at 37° C. The concentrations of the copolymer and free PEG were monitored at timed intervals by HPLC. For the solution in rat serum, the copolymer and PEG were first extracted with methylene chloride and then analyzed by HPLC, while for the solution in buffer, analysis was done directly by HPLC. Half-lives (t½) were calculated based on first order kinetics, as shown in Table 3. The data indicate that all of the tested polymers are degradable in both rat serum and phosphate buffer with varying degradation rates depending on the structure of the polymer. Larger PEG segments tended to result in longer degradation half-lives.

TABLE 3

Degradation Half-Lives (t1/2) of Selected Multi-Arm Block Copolymers

| Sample | In phosphate buffer (pH 7.0) | In rat serum |
|---|---|---|
| 8-arm-PLA-PEG5k | 365 h | 7 h |
| 8-arm-PLA-PEG2$_{6kDa}$ | 1251 h | 8 h |
| 8-arm-PCL-PEG5k | 643 d | 170 h |
| 8-arm-PCL-PEG2$_{6kDa}$ | 1010 d | 507 h |

EXAMPLE 13

Drug Release Studies Using PPO—PEG Multi-Arm Block Copolymers

In aqueous media, complexes of soluble lipophilic/hydrophobic drugs with the multi-arm PPO—PEG copolymer slowly release the drug. The water-insoluble drugs precipitate out of the formulation over time. Release profiles of the drugs were studied by determining the concentration of solubilized drug as a function of time at 23° C. At each time interval, aliquots were filtered through a 0.2 μm syringe filter and concentrations of drug measured by rp-HPLC or UV methods. For example, release of MNIPD from the soluble MNIPD/PPO—PEG formulation were measured by withdrawing 100 μl of solution, diluting to 1000 μl in water (at which point the drug dissolves), filtering through a 0.2 μm filter, and measuring absorbance of the filtrate at 465 nm. Drug release curves are presented in FIGS. 2–7.

In FIG. 2 is shown a comparison of the release rate of the drug, MNIPD, from PPO—PEG multi-arm copolymers 6035 and 6070 with the release rate of MNIPD from multi-arm PEGs (4-arm and 8-arm) and from Tween 80 (see Table 1). MNIPD was loaded into the polymers by Method I. After the MNIPD/polymer formulation was dissolved in phosphate buffer (0.1 M, pH 7), the release of the drug was followed by UV at 465 nm. The drug was released more slowly from copolymers 6035 and 6070 than from Tween 80. Solubility in the 4- and 8-arm PEGs was low and the drug was rapidly released from these polymers.

Release profiles of simvastatin from seven polymers are shown in FIG. 3. Simvastatin was loaded into the polymers by Method I. After dissolving in phosphate buffer (0.1 M, pH 7), the release of the drug was followed by HPLC. An extended release profile was observed from block copolymers 10050 and 10037 (see Table 1), while release from the PEGs (4-arm and 8-arm), 1307 and PPO—PEG 6035 was significantly more rapid. Solubility in the multi-arm PEG molecules and in PPO—PEG 6070 was very low.

In FIG. 4 is shown a release profile for simvastatin from PPO—PEG copolymer 10050 having a bisphosphonate targeting group attached to a distal terminus of the PEG moiety of the copolymer. Simvastatin was loaded into the bisphosphonate derivative of the copolymer by method I. After the drug/copolymer formulation dissolved in phosphate buffer (0.1 M, pH 7), the release of the drug was followed by HPLC. The drug was released over about 80 hours.

In FIG. 5 is shown a comparison of release profiles of paclitaxel from copolymer 10050 and from 8-arm PLA—PEG block copolymer. Paclitaxel was loaded into the copolymers by method I. After dissolving in phosphate buffer (0.1 M, pH 7), the release of the drug was followed by HPLC. Higher drug loading was possible with the 8-arm PLA—PEG copolymer.

In FIG. 6 is shown a comparison of release profiles of indomethacin from various copolymers. Indomethacin was loaded into the copolymers by Method I. After dissolving in phosphate buffer (0.1 M, pH 7), the release of the drug was followed by HPLC. Drug solubility was enhanced by the multi-arm block copolymers as well as by multi-arm PEG. Little or no release was observed from any of the polymers.

In FIG. 7 is shown comparative release profiles for pivaloyloxymethyl butyrate at two concentrations in PPO—PEG copolymers 10050 and 10037. Pivaloxymethyl butyrate was loaded into the copolymers by Method III. After dissolving in phosphate buffer (0.1 M, pH 7), the release of the drug was followed by HPLC. Extended release was observed from both polymers.

EXAMPLE 14

Release Profile of Cyclosporin A from Degradable 8-arm-PCL—PEG2$_{6kDa}$

The solution prepared in Example 9 was incubated at 37° C. At timed intervals, 10 μl of sample was withdrawn and diluted with phosphate buffer (0.1 M, pH 7.0). The solution was filtered through 0.2 μm syringe filter. The filtrate was analyzed by rp-HPLC for cyclosporin A concentration. The soluble cyclosporin A concentration in solution vs. time is shown in FIG. 8. The data illustrate the ability of the block copolymer to retain the cyclosporin A in solution for an extended period of time and to provide a controlled release of the drug.

EXAMPLE 15

Release Profile of Paclitaxel from Degradable 8-arm-PCL—PEG2$_{6kDa}$

The solution prepared in Example 10 was incubated at 37° C. At timed intervals, 10 μl of sample was withdrawn and diluted with phosphate buffer (0.1 M, pH 7.0). The solution was filtered through 0.2 μm syringe filter. The filtrate was analyzed by rp-HPLC for paclitaxel concentration. The soluble paclitaxel concentration in solution vs. time is shown in FIG. 9. The data illustrate the ability of the block copolymer to retain the paclitaxel in solution for an extended period of time and to provide a controlled release of the drug.

EXAMPLE 16

Antitumor Study of Paclitaxel-Loaded 8-arm PLA—mPEG$_{5kDa}$ in NCI-H460 Non-small Cell Lung Tumor Xenograft in Mice NCI-H460 non-small cell lung tumor was implanted subcutaneously in athymic nude mice. After the tumor grew to approximately 175 mg, the aqueous formulation of paclitaxel-loaded 8-arm PLA—mPEG$_{6kDa}$ was injected into mice via the tail vein. The mice were observed daily for survival. Tumor weights and body weights were recorded twice weekly. Each tumor was measured by caliper in two dimensions and converted to tumor mass using the formula for a prolate ellipsoid. For comparison, a standard formulation of Taxol® (in Cremophor®) and a control were also used. The results are shown in FIG. 10. The data indicate that the inhibition of tumor growth exhibited by the 8-arm PLA—mPEG block copolymer/drug formulation (referred to as UM-Paclitaxel in FIG. 10) was comparable to the standard Taxol® formulation.

EXAMPLE 17

Tolerance Study of Multi-Arm Block Copolymers in Mice

Dosages ranging from 500 to 2000 mg/kg/dose were intravenously administered to athymic nude mice for five days (days 1–5). As indicated in Table 4, all dosages were well tolerated.

TABLE 4

Tolerance study of multi-arm copolymers

| Unimolecular micelle polymers | Mean animal weight loss during 21 days | 21-day survival |
|---|---|---|
| 8-arm-PLA-PEG5k | <5% | All |
| 8-arm-PLA-PEG$_2$6k | <5% | All |
| 8-arm-PCL-PEG$_2$6k | <5% | All |

EXAMPLE 18

Dynamic Light Scattering Study

Micelle Preparation

A block copolymer (0.14 g) selected from the group including linear PEG—PLA, 8-arm-PLA—PEG5k, 8-arm-PLA—PEG2$_{6kDa}$, 8-arm-PCL—PEG5k, and 8-arm-PCL—PEG2$_{6kDa}$ was dissolved in 20 ml of N-dimethylacetamide (DMAc). The solution was warmed in order to dissolve the polymer easily. The solution was put into the pre-swollen dialysis membrane (Spectra/Pro1, MWCO 6000–8000) after 0.2 μm filtration. Dialysis was carried out against deionized water for 24 h. Water was changed at 1, 2, 4 and 7 hours from the beginning. The prepared micelle solution was stored at 4° C. until use.

Micelles Loaded with Paclitaxel

Taxol® was loaded into the micelle solution in two ways. Method 1: To the micelle solution (10 ml) prepared as described above was added 0.5 ml of paclitaxel solution in CHCl$_3$ (4 mg/mL) dropwisely. After 16 h of vigorous stirring, CHCl$_3$ was removed from the solution by aspiration. The solution was filtered through 0.2 μm membrane. Method 2: Block copolymer (0.14 g) and paclitaxel (5 mg) were dissolved in DMAc and dialyzed as described above. After dialysis, the solution was filtered with 0.2 μm membrane.

Dynamic Light Scattering (DLS)

The size and the distribution of micelles were measured by dynamic light scattering. The sample was filtered with 0.2 μm pore-size membrane prior to the measurement. The measurement was carried out at 25° C. Size and polydispersity of the particle was determined by cumulant analysis method based on the assumption that the micelles were spherical. FIG. 11 provides an example of dynamic light scattering results. Tables 5, 6 and 7 provide micelle sizes and polydispersity for micelles with and without paclitaxel loading as determined by light scattering.

TABLE 5

Size of Micelles Determined by Light Scattering

| Sample | Effective Diameter (nm) | Polydispersity | Count Rate |
|---|---|---|---|
| Linear PEG-PLA | 30.4 | 0.198 | 313.8 |
| 8-arm-PLA-PEG5k | 47.0 | 0.291 | 123.5 |
| 8-arm-PLA-PEG2$_{6kDa}$ | 100.7 | 0.351 | 251.9 |
| 8-arm-PCL-PEG5k | 24.9 | 0.066 | 101.2 |
| 8-arm-PCL-PEG2$_{6kDa}$ | 19.3 | 0.079 | 73.3 |

TABLE 6

Size of Micelles Loaded with Paclitaxel Prepared by Method 1

| Sample | Effective Diameter (nm) | Polydispersity | Count Rate |
|---|---|---|---|
| Linear PEG-PLA | 39.1 | 0.226 | 363.0 |
| 8-arm-PLA-PEG5k | | | |
| 8-arm-PLA-PEG2$_{6kDa}$ | | | |
| 8-arm-PCL-PEG5k | 49.0 | 0.106 | 692.0 |
| 8-arm-PCL-PEG2$_{6kDa}$ | 26.2 | 0.177 | 153.3 |

TABLE 7

Size of Micelles Loaded with Paclitaxel Prepared by Method 2

| Sample | Effective Diameter (nm) | Polydispersity | Count Rate |
|---|---|---|---|
| Linear PEG-PLA | 31.8 | 0.246 | 312.3 |
| 8-arm-PLA-PEG5k | | | |
| 8-arm-PLA-PEG2$_{6kDa}$ | 86.4 | 0.342 | 235.7 |
| 8-arm-PCL-PEG5k | | | |
| 8-arm-PCL-PEG2$_{6kDa}$ | 19.7 | 0.064 | 77.3 |

The above data indicate that the effective diameter of the multi-arm block copolymer structure increases after loading with the drug.

EXAMPLE 19

Evaluation of Micelle Aggregates by Dynamic Light Scattering

Micelle solutions of BCD—PCL—PEG2$_{6kDa}$, 8-arm-PCL—PEG2$_{6kDa}$, and linear PEG—PCL (MW 5,000—5,000) were prepared by a dialysis method. For linear PEG—PLA, the polymer solution in DMAc was mixed with water by dropwise adding 20 mL of water to the polymer solution prior to the dialysis in order to avoid the formation of aggregation. The concentration of micelle solutions was in the range of 2.88–3.34 mg/ml (see Table 8).

The micelle solutions were treated with ~2.5 ml of 5% SDS solution for 24 hours. The micelle solutions before and after the addition of surfactant (SDS) were characterized after filtration through 0.2 μm syringe filter using a Brookhaven 90 Plus Particle Sizer. Table 4 summarizes the DLS cumulant analysis results. The cumulant diameter of the micelles ranged from 19 to 35 nm before the SDS addition. The DLS measurement was also carried out without filtration, and little alteration of micelle property was seen on the multi-arm block copolymers. BCD—PCL—PEG2$_{6kDa}$ had the least change in micelle property before and after SDS addition. The other micelles presented dramatic change in size and significant decrease in count rate. The count rate of the BCD—PCL—PEG2$_{6kDa}$ micelles was reduced by 30%. This was likely due to the dilution of the micelle solution rather than the dissociation of micelles. Multi-armed PEG block copolymers with higher number of arms tend to be less aggregated.

The data tends to suggest that increases in the number of arms of the multi-arm block copolymers of the present invention reduces the tendency of the hydrophobic cores of the copolymers to aggregate in the same manner as conventional linear micelles. Since less aggregation occurs with multi-arm copolymers with a greater number of arms, less disaggregation is caused by addition of the surfactant. In contrast, smaller block copolymers of the invention and linear micelles tend to aggregate to a greater extent, thereby resulting in a measurable disruption in aggregation by the surfactant.

TABLE 8

DLS cumulant analysis results of BCD-PCL-(PEG3k)$_2$, 8-arm-PCL-PEG2$_{6kDa}$, and linear PEG-PCL micelles

| Samples | Concentration (mg/mL) | Diameter (nm) | Dispersity | Count rate (kcps) | % Count Remaining |
|---|---|---|---|---|---|
| BCD-PCL-PEG2$_{6kDa}$ 2 Before filter | 3.34 | 19.8 | 0.098 | 52.7 | |
| BCD-PCL-PEG2$_{6kDa}$ After filter | 3.34 | 19.4 | 0.058 | 44.2 | |
| BCD-PCL-PEG2$_{6kDa}$ + SDS | 3.34 | 22.7 | 0.152 | 30.7 | 69.45701357 |
| 8-arm-PCL-PEG2$_{6kDa}$ Before filter | 3.24 | | | | |
| 8-arm-PCL-PEG2$_{6kDa}$ After filter | 3.24 | 26.8 | 0.158 | 107.1 | |
| 8-arm-PCL-PEG2$_{6kDa}$ + SDS | 3.24 | 42.2 | 0.24 | 23.5 | 21.94211018 |
| Linear PEG-PCL Before filter | 2.88 | | | | |
| Linear PEG-PCL After filter | 2.88 | 35.6 | 0.006 | 348.7 | |
| Linear PEG-PCL + SDS | 2.88 | 11 | 0.401 | 11 | 3.154574132 |

Many modifications and other embodiments of the invention will come to mind to one skilled in the art to which this invention pertains having the benefit of the teachings presented in the foregoing descriptions and the associated tables. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A multi-arm block copolymer useful as a drug delivery vehicle, comprising a central core molecule comprising a residue of a polyol, and at least three copolymer arms covalently attached to the central core molecule, each copolymer arm comprising an inner hydrophobic polymer segment covalently attached to the central core molecule and an outer hydrophilic polymer segment covalently attached to the hydrophobic polymer segment, wherein the central core molecule and the hydrophobic polymer segment define a hydrophobic core region, and wherein the hydrophilic polymer segment comprises a poly(hydroxyester).

2. The multi-arm block copolymer of claim 1, wherein the central core molecule is a residue of a polyol comprising 3 to about 25 hydroxyl groups.

3. The multi-arm block copolymer of claim 2, wherein the central core molecule is a residue of a polyol comprising 3 to about 8 hydroxyl groups.

4. The multi-arm block copolymer of claim 2, wherein the central core molecule is a residue of a polyol selected from the group consisting of glycerol, hexaglycerol, sorbitol, pentaerythritol, and hydroxypropyl-β-cyclodextrin.

5. The multi-arm block copolymer of claim 1, wherein the inner hydrophobic polymer segment comprises a poly(hydroxyester) selected from the group consisting of poly(lactide), poly(glycolide), poly(lactide)/(glycolide) copolymer, poly(butyrolactide), and polycaprolactone.

6. The multi-arm block copolymer of claim 1, wherein the outer hydrophilic polymer segment comprises poly(ethylene glycol).

7. The multi-arm block copolymer of claim 1, wherein each hydrophobic and hydrophilic polymer segment has a molecular weight of about 500 Da to about 100,000 Da.

8. The multi-arm block copolymer of claim 1, wherein each hydrophobic polymer segment has a molecular weight of about 10,000 Da to about 40,000 Da.

9. The multi-arm block copolymer of claim 1, wherein each hydrophilic polymer segment has a molecular weight of about 1,000 Da to about 20,000 Da.

10. The multi-arm block copolymer of claim 1, wherein the central core molecule is attached to at least 5 copolymer arms.

11. The multi-arm block copolymer of claim 1, wherein the central core molecule is attached to at least 8 copolymer arms.

12. The multi-arm copolymer of claim 1, wherein the central core molecule is attached to 3 to about 8 copolymer arms.

13. The multi-arm block copolymer of claim 1, wherein at least one targeting moiety is covalently attached to at least one hydrophilic polymer segment.

14. The multi-arm block copolymer of claim 13, wherein the targeting moiety is selected from the group consisting of a protein, an antibody, an antibody fragment, a peptide, a carbohydrate, a lipid, an oligonucleotide, DNA, RNA, and a small molecule having molecular weight less than 2000 Daltons.

15. The multi-arm block copolymer of claim 13, wherein the targeting moiety is a bisphosphonate.

16. The multi-arm block copolymer of claim 1, wherein at least one capping group or functional group is covalently attached to at least one hydrophilic polymer segment.

17. The multi-arm block copolymer of claim 16, wherein the capping group or functional group is selected from the group consisting of alkoxy, hydroxyl, protected hydroxyl, active ester, active carbonate, acetal, aldehyde, aldehyde hydrate, alkyl or aryl sulfonate, halide, disulfide, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxal, dione, mesylate, tosylate, and tresylate.

18. The multi-arm block copolymer of claim 1, having the structure:

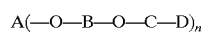

wherein:

A is a central core molecule comprising a residue of a polyol,

O is oxygen,

B is a hydrophobic polymer segment comprising a poly (hydroxyester),

C is a hydrophilic polymer segment,

D is a capping group or functional group, and n is 3 to about 25.

19. The multi-arm block copolymer of claim 18, wherein each D is alkoxy.

20. The multi-arm block copolymer of claim 18, wherein each D is hydroxy.

21. The multi-arm block copolymer of claim 18, wherein each D is selected from the group consisting of alkoxy, hydroxyl, protected hydroxyl, active ester, active carbonate, acetal, aldehyde, aldehyde hydrate, alkyl or aryl sulfonate, halide, disulfide, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxal, dione, mesylate, tosylate, and tresylate.

22. The multi-arm block copolymer of claim 18, wherein A is a residue of a polyol selected from the group consisting of glycerol, hexaglycerol, sorbitol, pentaerythritol, and hydroxypropyl-β-cyclodextrin.

23. The multi-arm block copolymer of claim 18, wherein at least one of B and C comprises at least one degradable linkage.

24. The multi-arm block copolymer of claim 18, wherein C comprises poly(ethylene glycol).

25. The multi-arm block copolymer of claim 1, having the structure:

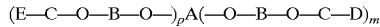

(E—C—O—B—O—)$_p$A(—O—B—O—C—D)$_m$ wherein:

A is a central core molecule moiety comprising a residue of a polyol,

O is oxygen,

B is a hydrophobic polymer segment comprising a poly (hydroxyester),

C is a hydrophilic polymer segment,

D is a hydroxyl or alkoxy group, p is at least 1, the sum of m and p is from 3 to about 25, and E is a functional group selected from the group consisting of active ester, active carbonate, acetal, aldehyde, aldehyde hydrate, alkyl or aryl sulfonate, halide, disulfide, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxal, dione, mesylate, tosylate, and tresylate.

26. The multi-arm block copolymer of claim 1, having the structure:

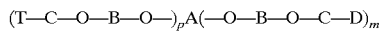

(T—C—O—B—O—)$_p$A(—O—B—O—C—D)$_m$ wherein:

A is a central core molecule moiety comprising a residue of a polyol,

O is oxygen,

B is a hydrophobic polymer segment comprising a poly (hydroxyester),

C is a hydrophilic polymer segment,

D is a capping group, p is at least 1, the sum of m and p is from 3 to about 25, and T is a targeting moiety.

27. The multi-arm block copolymer of claim 26, wherein T is selected from the group consisting of a protein, an antibody, an antibody fragment, a peptide, a carbohydrate, a lipid, an oligonucleotide, DNA, RNA, and a small molecule having molecular weight less than 2000 Daltons.

28. The multi-arm block copolymer of claim 26, wherein T is a bisphosphonate.

29. The multi-arm block copolymer of claim 1, having the structure:

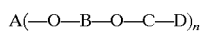

A(—O—B—O—C—D)$_n$ wherein:

A is a central core molecule comprising a residue of a polyol having 3 to about 8 hydroxyl groups, O is oxygen, B is a hydrophobic polymer segment comprising a poly (hydroxyester), C is a hydrophilic polymer segment comprising poly (ethylene glycol), D is a capping group or functional group, and n is 3 to about 8.

30. The multi-arm block copolymer of claim 29, wherein each D is alkoxy or hydroxyl.

31. The multi-arm block copolymer of claim 29, wherein A is a residue of a polyol selected from the group consisting of glycerol, hexaglycerol, sorbitol, and pentaerythritol.

32. The multi-arm block copolymer of claim 29, wherein at least one of B and C comprises at least one degradable linkage.

33. A multi-arm block copolymer useful as a drug delivery vehicle, comprising a central core molecule comprising a residue of a polyol having at least 3 hydroxyl groups, and at least three copolymer arms covalently attached to the central core molecule, each copolymer arm comprising an inner hydrophobic polymer segment covalently attached to the central core molecule and an outer hydrophilic polymer segment covalently attached to the hydrophobic polymer segment, wherein the central core molecule and the hydrophobic polymer segment define a hydrophobic core region, and wherein the hydrophobic polymer segment is a poly (hydroxyester) and the hydrophilic polymer segment is poly(ethylene glycol).

34. The multi-arm block copolymer of claim 33, wherein the central core molecule is a residue of a polyol comprising 3 to about 8 hydroxyl groups.

35. The multi-arm block copolymer of claim 34, wherein the central core molecule is a residue of a polyol selected from the group consisting of glycerol, hexaglycerol, sorbitol, and pentaerythritol.

36. The multi-arm block copolymer of claim 33, wherein the inner hydrophobic polymer segment is a poly (hydroxyester) selected from the group consisting of poly (lactide), poly(glycolide), poly(lactide)/(glycolide) copolymer, poly(butyrolactide), and polycaprolactone.

37. A multi-arm block copolymer useful as a drug delivery vehicle, comprising a central core molecule comprising a residue of a polyol having 3 to about 8 hydroxyl groups, and 3 to about 8 copolymer arms covalently attached to the central core molecule, each copolymer arm comprising an inner hydrophobic polymer segment covalently attached to the central core molecule and an outer hydrophilic polymer segment covalently attached to the hydrophobic polymer segment, wherein the central core molecule and the hydrophobic polymer segment define a hydrophobic core region, and wherein the hydrophobic polymer segment is a poly(hydroxyester) having a number average molecular weight of about 500 Da to about 40,000 Da and the hydrophilic polymer segment is a linear or branched poly(ethylene glycol) having a number average molecular weight of about 500 Da to about 100,000 Da.

38. The multi-arm block copolymer of claim 37, having the structure:

$$A(-O-B-O-C-D)_n$$

wherein:
A is a central core molecule comprising a residue of a polyol having 3 to about 8 hydroxyl groups,
O is oxygen,
B is a poly(hydroxyester) having a number average molecular weight of about 500 Da to about 40,000 Da,
C is a linear or branched poly(ethylene glycol) having a number average molecular weight of about 500 Da to about 100,000 Da,
D is alkoxy or hydoxyl,
and n is 3 to about 8.

* * * * *